(12) United States Patent
Ushiroda et al.

(10) Patent No.: US 12,295,543 B2
(45) Date of Patent: May 13, 2025

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventors: Hiroshi Ushiroda, Tokyo (JP); Toshiyuki Sasaki, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 91 days.

(21) Appl. No.: 18/247,748

(22) PCT Filed: Aug. 19, 2021

(86) PCT No.: PCT/JP2021/030443
§ 371 (c)(1),
(2) Date: Apr. 4, 2023

(87) PCT Pub. No.: WO2022/080008
PCT Pub. Date: Apr. 21, 2022

(65) Prior Publication Data
US 2023/0346196 A1    Nov. 2, 2023

(30) Foreign Application Priority Data

Oct. 15, 2020   (JP) ................................ 2020-174245

(51) Int. Cl.
*A61B 1/00* (2006.01)
*A61B 1/005* (2006.01)
(Continued)

(52) U.S. Cl.
CPC ...... *A61B 1/00009* (2013.01); *A61B 1/00188* (2013.01); *A61B 1/005* (2013.01);
(Continued)

(58) Field of Classification Search
CPC . A61B 1/00009; A61B 1/00188; A61B 1/005; A61B 1/045; A61B 90/361;
(Continued)

(56) References Cited

U.S. PATENT DOCUMENTS

| 2012/0209123 A1* | 8/2012 | King | A61B 1/0005 |
| | | | 600/476 |
| 2015/0146011 A1* | 5/2015 | Tsubusaki | G06V 40/161 |
| | | | 348/169 |

(Continued)

FOREIGN PATENT DOCUMENTS

| JP | 2012-166024 A | 9/2012 |
| JP | 2015-102853 A | 6/2015 |

(Continued)

OTHER PUBLICATIONS

International Search Report and Written Opinion mailed on Nov. 9, 2021, received for PCT Application PCT/JP2021/030443, filed on Aug. 19, 2021, 14 pages including English Translation.

*Primary Examiner* — Michael E Teitelbaum
(74) *Attorney, Agent, or Firm* — XSENSUS LLP

(57) ABSTRACT

A medical image processing device 3 includes: a captured image acquisition unit 31 that acquires a captured image captured by a medical observation device 2; a determination unit 33 that determines whether or not an imaging field of view of the medical observation device 2 has been moved; and an identification image generation unit 321 that generates, in a case where the determination unit 33 determines that the imaging field of view has been moved, an identification image in which a specific position in a specific region displayed on a display device in an entire image region of the captured image is identifiable with respect to other positions.

20 Claims, 13 Drawing Sheets

(51) Int. Cl.
  *A61B 1/045* (2006.01)
  *A61B 90/00* (2016.01)
  *G06V 20/69* (2022.01)

(52) U.S. Cl.
  CPC ............ *A61B 1/045* (2013.01); *A61B 90/361* (2016.02); *G06V 20/69* (2022.01)

(58) Field of Classification Search
  CPC ... A61B 1/00006; A61B 1/0005; A61B 90/25; A61B 90/30; A61B 90/20; G06V 20/69; G06V 2201/03; G06V 40/197
  See application file for complete search history.

(56) References Cited

U.S. PATENT DOCUMENTS

| | | |
|---|---|---|
| 2017/0042407 A1* | 2/2017 | Miyai .................... G16H 30/20 |
| 2017/0046842 A1* | 2/2017 | Yamaguchi ...... A61B 1/000095 |
| 2019/0107699 A1 | 4/2019 | Iida |
| 2019/0290384 A1 | 9/2019 | Yamaguchi |
| 2020/0179078 A1* | 6/2020 | Tsukashima ........... A61B 90/37 |

FOREIGN PATENT DOCUMENTS

| | | |
|---|---|---|
| JP | 2017-038285 A | 2/2017 |
| JP | 2019-154886 A | 9/2019 |
| JP | 2019-166156 A | 10/2019 |
| WO | 2016/199273 A1 | 12/2016 |
| WO | 2017/169650 A1 | 10/2017 |
| WO | 2020/080209 A1 | 4/2020 |

\* cited by examiner

FIG.8
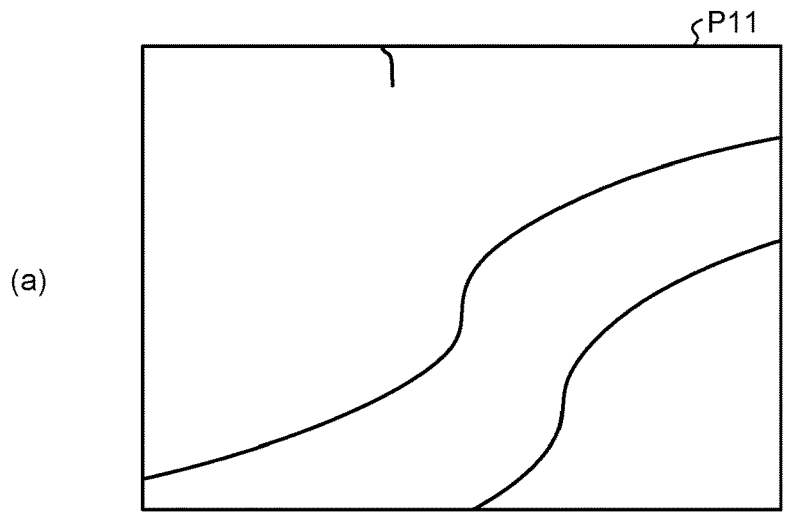
(a)
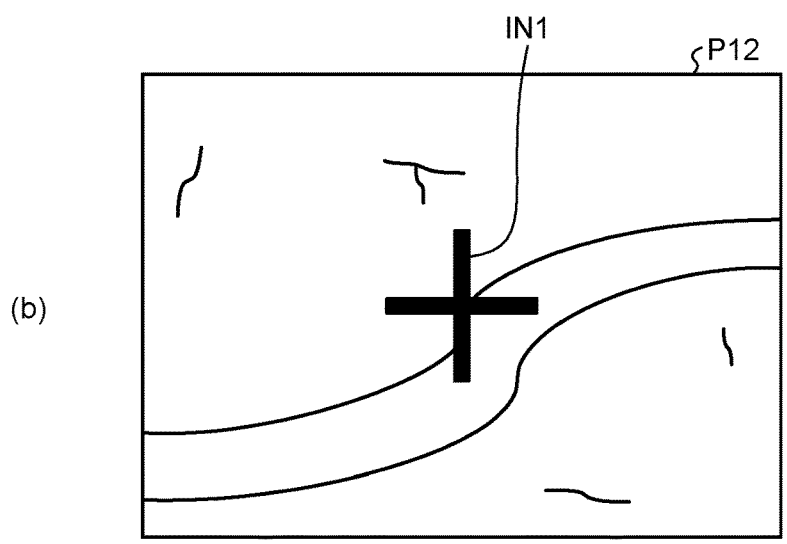
(b)
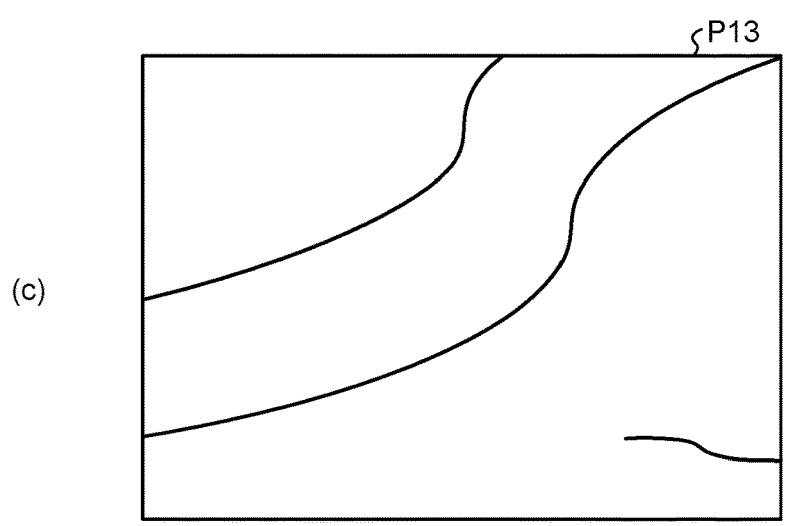
(c)

FIG.13
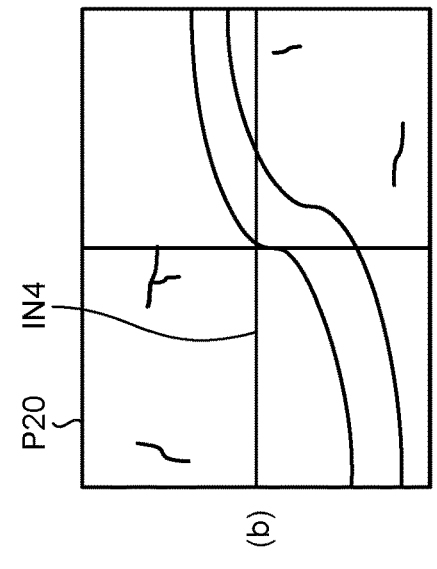
(b)
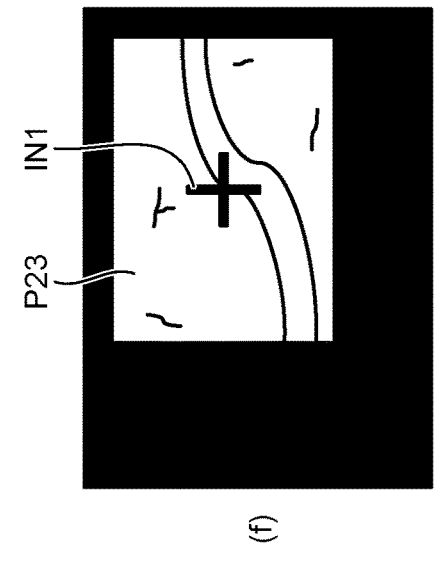
(f)
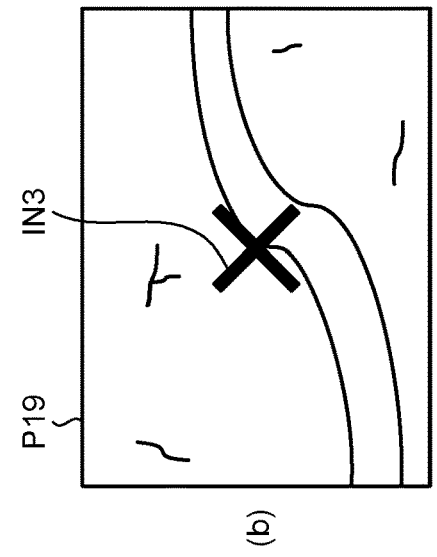
(b)
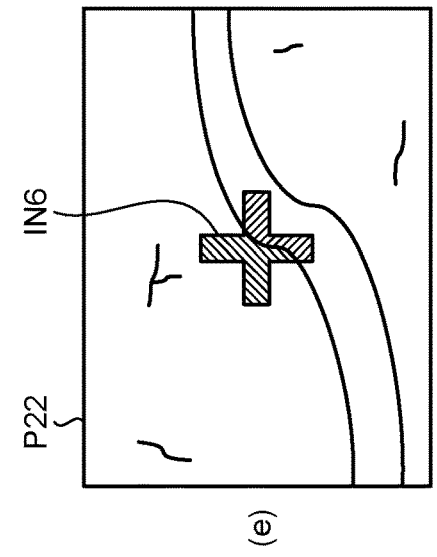
(e)
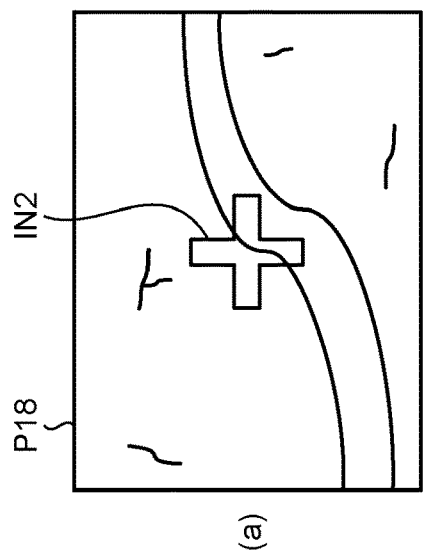
(a)
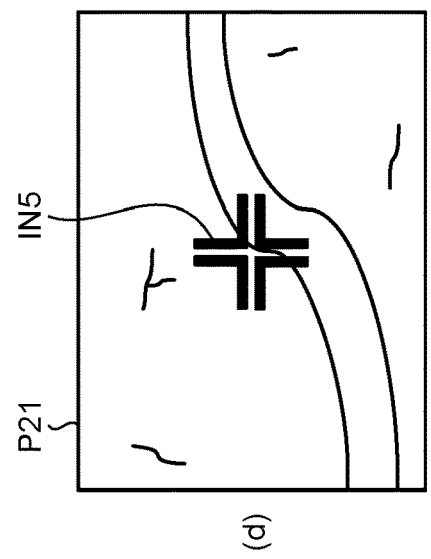
(d)

MEDICAL IMAGE PROCESSING DEVICE AND MEDICAL OBSERVATION SYSTEM

CROSS-REFERENCE TO RELATED APPLICATIONS

The present application is based on PCT filing PCT/JP2021/030443, filed Aug. 19, 2021, which claims priority to JP 2020-174245, filed Oct. 15, 2020, the entire contents of each are incorporated herein by reference.

FIELD

The present disclosure relates to a medical image processing device and a medical observation system.

BACKGROUND

Hitherto, a medical observation system that images an observation target (subject) and displays a captured image obtained by the imaging in order to support microsurgery such as neurosurgery has been known (see, for example, Patent Literature 1).

The medical observation system described in Patent Literature 1 includes a microscope unit that images a subject to generate a captured image, and a support unit that supports the microscope unit rotatably around a plurality of axes different from each other. Then, an observer manually or electrically changes a posture of the support unit in order to image a part to be observed with the microscope unit.

CITATION LIST

Patent Literature

Patent Literature 1: JP 2019-166156 A

SUMMARY

Technical Problem

However, in the medical observation system described in Patent Literature 1, even in a case where the observer manually or electrically changes the posture of the support unit in a state of gazing at the displayed captured image, it is difficult for the observer to position the part to be observed at a specific position (for example, a center position) in the captured image.

Therefore, there is a demand for a technology capable of easily positioning a part to be observed at a specific position in a captured image and improving convenience.

The present disclosure has been made in view of the above, and an object of the present disclosure is to provide a medical image processing device and a medical observation system capable of improving convenience.

Solution to Problem

To solve the above-described problem and achieve the object, a medical image processing device according to the present disclosure includes: a captured image acquisition unit configured to acquire a captured image captured by a medical observation device; a determination unit configured to determine whether or not an imaging field of view in the medical observation device has been moved; and an identification image generation unit configured to generate, in a case where the determination unit determines that the imaging field of view has been moved, an identification image in which a specific position in a specific region displayed on a display device in an entire image region of the captured image is identifiable with respect to other positions.

A medical image processing device according to the present disclosure includes: a captured image acquisition unit configured to acquire a captured image captured by a medical observation device; an operating unit configured to receive a moving operation for an imaging field of view in the medical observation device; and an identification image generation unit configured to generate, in a case where the operating unit has received the moving operation, an identification image in which a specific position in a specific region displayed on a display device in an entire image region of the captured image is identifiable with respect to other positions.

A medical observation system according to the present disclosure includes: a medical observation device configured to generate a captured image by imaging a subject; a medical image processing device; and a display device configured to display an identification image generated by the medical image processing device, wherein the medical image processing device includes: a captured image acquisition unit configured to acquire the captured image; a determination unit configured to determine whether or not an imaging field of view in the medical observation device has been moved; and an identification image generation unit configured to generate, in a case where the determination unit determines that the imaging field of view has been moved, the identification image in which a specific position in a specific region displayed on the display device in an entire image region of the captured image is identifiable with respect to other positions.

Advantageous Effects of Invention

With the medical image processing device and the medical observation system according to the present disclosure, convenience can be improved.

BRIEF DESCRIPTION OF DRAWINGS

FIG. 8 is a view illustrating an identification image according to a fifth embodiment.

FIG. 13 is a view illustrating modifications of the first to tenth embodiments.

DESCRIPTION OF EMBODIMENTS

Hereinafter, embodiments for carrying out the present disclosure (hereinafter, referred to as embodiments) will be described with reference to the drawings. Note that the present disclosure is not limited to the embodiments described below. Further, in the description of the drawings, the same reference signs denote the same parts.

First Embodiment

[Schematic Configuration of Medical Observation System]

Figure 1:
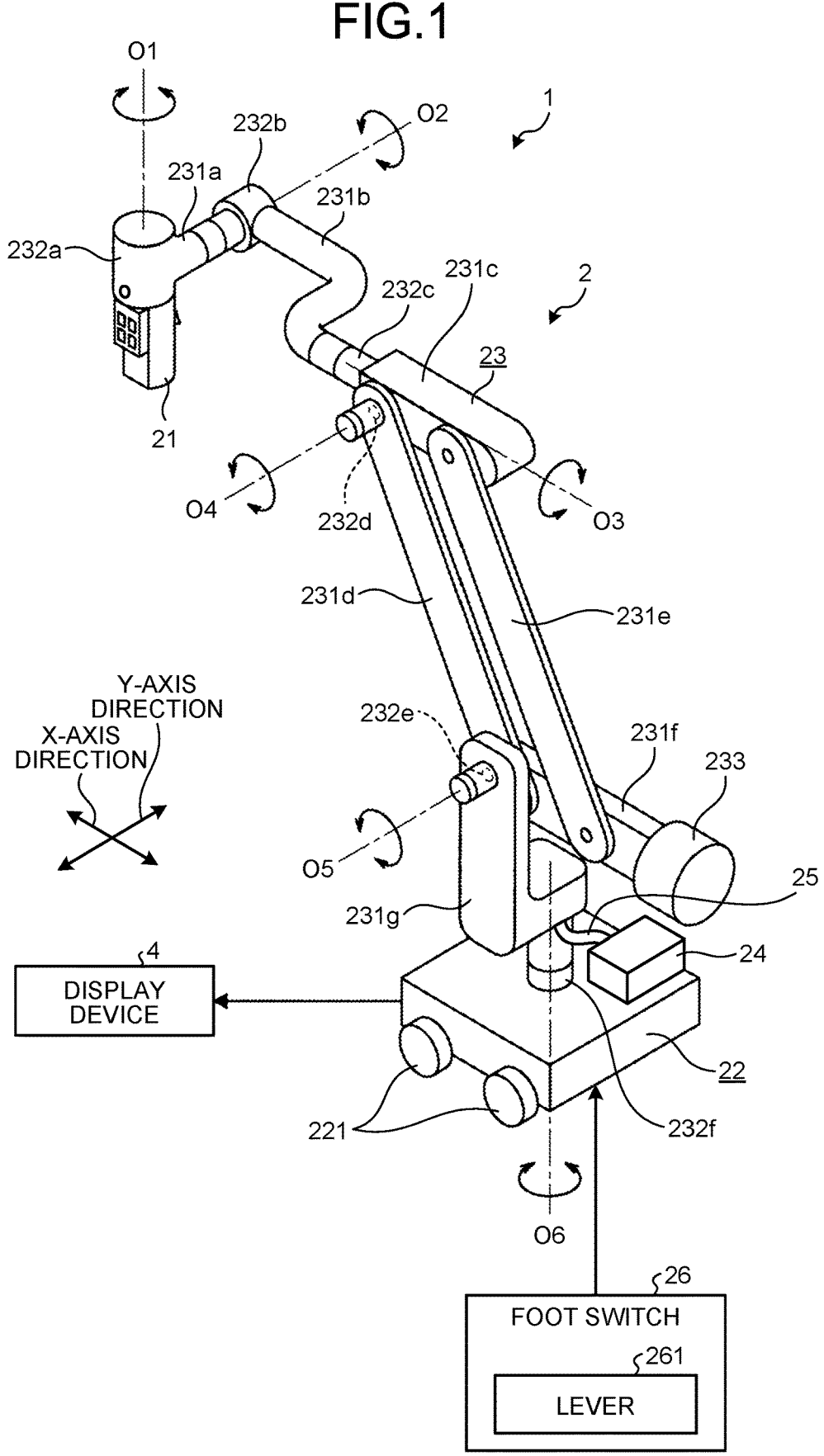
FIG. 1 is a view illustrating a medical observation system according to a first embodiment.
Figure 2:
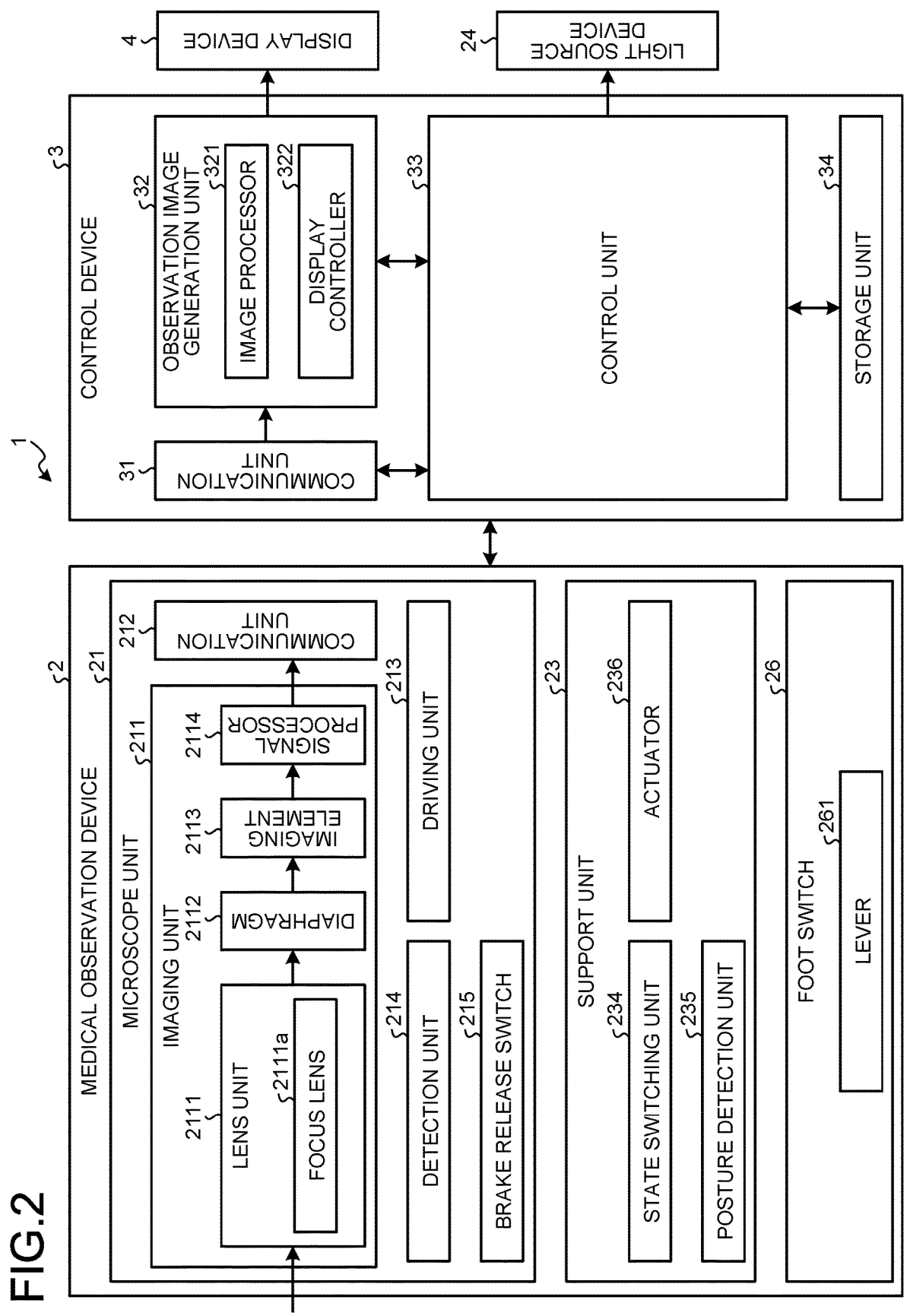
FIG. 2 is a block diagram illustrating the medical observation system.

FIG. 1 is a diagram illustrating a medical observation system 1 according to a first embodiment. FIG. 2 is a block diagram illustrating the medical observation system 1.

The medical observation system 1 is a system that images an observation target (subject) and displays a captured image obtained by the imaging in order to support microsurgery such as neurosurgery or perform endoscopic surgery, for example. As illustrated in FIG. 1 or 2, the medical observation system 1 includes a medical observation device 2 that images the observation target, a control device 3 that processes a captured image obtained by the imaging performed by the medical observation device 2, and a display device 4 that displays the captured image processed by the control device 3.

[Configuration of Medical Observation Device]

The medical observation device 2 is a surgical microscope that enlarges and captures an image of a predetermined field of view of the observation target, and includes a microscope unit 21, a base unit 22 (FIG. 1), a support unit 23, a light source device 24, a light guide 25 (FIG. 1), and a foot switch 26 as illustrated in FIG. 1 or 2.

As illustrated in FIG. 2, the microscope unit 21 includes an imaging unit 211, a communication unit 212, a driving unit 213, a detection unit 214, and a brake release switch 215.

The imaging unit 211 is a portion that images the observation target to generate the captured image. As illustrated in FIG. 2, the imaging unit 211 includes a lens unit 2111, a diaphragm 2112, an imaging element 2113, and a signal processor 2114.

The lens unit 2111 includes a focus lens 2111a (FIG. 2), takes in a subject image from the observation target, and forms the subject image on an imaging surface of the imaging element 2113.

The focus lens 2111a includes one or more lenses, and adjusts a focal position by moving along an optical axis.

Further, a focus mechanism (not illustrated) for moving the focus lens 2111a along the optical axis is provided in the lens unit 2111.

The diaphragm 2112 is provided between the lens unit 2111 and the imaging element 2113, and adjusts a light amount of the subject image from the lens unit 2111 toward the imaging element 2113 under the control of the control device 3.

Here, the driving unit 213 operates the above-described focus mechanism under the control of the control device 3 in AF processing as described later to adjust a focal position of the lens unit 2111, the AF processing being performed by the control device 3. In addition, the driving unit 213 operates the diaphragm 2112 under the control of the control device 3 to adjust a diaphragm value of the diaphragm 2112.

The detection unit 214 includes a position sensor such as a photo interrupter, and detects a current position (focal position) of the focus lens 2111a. Further, the detection unit 214 outputs a signal corresponding to the detected focal position to the control device 3. Furthermore, the detection unit 214 includes a linear encoder and the like, and detects the current diaphragm value of the diaphragm 2112. Then, the detection unit 214 outputs a signal corresponding to the detected diaphragm value to the control device 3.

The imaging element 2113 is implemented by an image sensor that receives the subject image formed by the lens unit 2111 and generates a captured image (analog signal).

The signal processor 2114 performs signal processing on the captured image (analog signal) generated by the imaging element 2113.

For example, the signal processor 2114 performs, on the captured image (analog signal) generated by the imaging element 2113, processing of removing reset noise, processing of multiplying an analog gain for amplifying the analog signal, and signal processing such as A/D conversion.

The communication unit 212 is an interface that communicates with the control device 3, transmits the captured image (digital signal) subjected to the signal processing performed by the signal processor 2114 to the control device 3, and receives a control signal from the control device 3.

The function of the brake release switch 215 will be described together with the configuration of the control device 3 for convenience of explanation.

The base unit 22 is a base of the medical observation device 2, and is configured to be movable on a floor surface via casters 221 (FIG. 1).

The support unit 23 extends from the base unit 22 and holds the microscope unit 21 at a distal end (an end portion positioned away from the base unit 22). Then, the support unit 23 enables the microscope unit 21 to move three-dimensionally.

In the first embodiment, the support unit 23 has six degrees of freedom for movement of the microscope unit 21, but is not limited thereto, and may have a different number of degrees of freedom.

As illustrated in FIG. 1 or 2, the support unit 23 includes first to seventh arms 231a to 231g, first to sixth joints 232a to 232f, a state switching unit 234, a posture detection unit 235, and an actuator 236.

The first joint 232a is positioned at the distal end of the support unit 23. The first joint 232a holds the microscope unit 21 in such a way as to be rotatable around a first axis O1 (FIG. 1) while being fixedly supported by the first arm 231a.

Here, the first axis O1 coincides with an observation optical axis of the microscope unit 21. That is, when the microscope unit 21 rotates around the first axis O1, a direction of an imaging field of view of the microscope unit 21 is changed.

The first arm 231a is a substantially rod-shaped member extending in a direction orthogonal to the first axis O1, and fixedly supports the first joint 232a at a distal end thereof.

The second joint 232b holds the first arm 231a in such a way as to be rotatable around a second axis O2 (FIG. 1) while being fixedly supported by the second arm 231b. Therefore, the second joint 232b enables the microscope unit 21 to rotate around the second axis O2.

Here, the second axis O2 is orthogonal to the first axis O1 and is parallel to an extending direction of the first arm 231a. That is, when the microscope unit 21 rotates around the second axis O2, a direction of the observation optical axis of the microscope unit 21 with respect to the observation target is changed. In other words, the imaging field of view of the microscope unit 21 is moved along an X axis (FIG. 1) orthogonal to the first and second axes O1 and O2 in a horizontal plane. Therefore, the second joint 232b is a joint for moving the imaging field of view of the microscope unit 21 along the X axis.

The second arm 231b has a crank shape extending in a direction orthogonal to the first and second axes O1 and O2, and fixedly supports the second joint 232b at a distal end thereof.

The third joint 232c holds the second arm 231b in such a way as to be rotatable around a third axis O3 (FIG. 1) while being fixedly supported by the third arm 231c. Therefore, the third joint 232c enables the microscope unit 21 to rotate around the third axis O3.

Here, the third axis O3 is orthogonal to the first and second axes O1 and O2. That is, when the microscope unit 21 rotates around the third axis O3, the direction of the observation optical axis of the microscope unit 21 with respect to the observation target is changed. In other words, the imaging field of view of the microscope unit 21 is moved along a Y axis (FIG. 1) orthogonal to the X axis in the horizontal plane. Therefore, the third joint 232c is a joint for moving the imaging field of view of the microscope unit 21 along the Y axis.

The third arm 231c is a substantially rod-shaped member extending in a direction substantially parallel to the third axis O3, and fixedly supports the third joint 232c at a distal end thereof.

The fourth joint 232d holds the third arm 231c in such a way as to be rotatable around a fourth axis O4 (FIG. 1) while being fixedly supported by the fourth arm 231d. Therefore, the fourth joint 232d enables the microscope unit 21 to rotate around the fourth axis O4.

Here, the fourth axis O4 is orthogonal to the third axis O3. That is, when the microscope unit 21 rotates around the fourth axis O4, a height of the microscope unit 21 is adjusted. Therefore, the fourth joint 232d is a joint for moving the microscope unit 21 in a parallel direction.

The fourth arm 231d is a substantially rod-shaped member that is orthogonal to the fourth axis O4 and linearly extends toward the base unit 22, and fixedly supports the fourth joint 232d on one end side.

The fifth arm 231e has the same shape as the fourth arm 231d. One end side of the fifth arm 231e is connected to the third arm 231c in such a way as to be rotatable around an axis parallel to the fourth axis O4.

The sixth arm 231f has substantially the same shape as the third arm 231c. The sixth arm 231f is connected to the other end sides of the fourth and fifth arms 231d and 231e in such a way as to be rotatable around an axis parallel to the fourth axis O4 in a posture forming a parallelogram with the third to fifth arms 231c to 231e. A counterweight 233 (FIG. 1) is provided at an end portion of the sixth arm 231f.

A mass and an arrangement position of the counterweight 233 are adjusted in such a way that a rotational moment generated around the fourth axis O4 and a rotational moment generated around a fifth axis O5 (FIG. 1) can be offset by mass of components provided more adjacent to a distal end side of the support unit 23 (a side on which the microscope unit 21 is provided) than the counterweight 233 is. That is, the support unit 23 is a balance arm (a configuration in which the counterweight 233 is provided). The support unit 23 may have a configuration in which the counterweight 233 is not provided.

The fifth joint 232e holds the fourth arm 231d in such a way as to be rotatable around the fifth axis O5 while being fixedly supported by the seventh arm 231g. Therefore, the fifth joint 232e enables the microscope unit 21 to rotate around the fifth axis O5.

Here, the fifth axis O5 is parallel to the fourth axis O4. That is, when the microscope unit 21 rotates around the fifth axis O5, the height of the microscope unit 21 is adjusted. Therefore, the fifth joint 232e is a joint for moving the microscope unit 21 in a parallel direction.

The seventh arm 231g has a substantially L shape including a first portion extending in a vertical direction and a second portion extending while being bent substantially at a right angle with respect to the first portion, and fixedly supports the fifth joint 232e at the first portion.

The sixth joint 232f holds the second portion of the seventh arm 231g in such a way as to be rotatable around a sixth axis O6 (FIG. 1) while being fixedly supported by the base unit 22. Therefore, the sixth joint 232f enables the microscope unit 21 to rotate around the sixth axis O6.

Here, the sixth axis O6 is an axis along the vertical direction. That is, the sixth joint 232f is a joint for moving the microscope unit 21 in a parallel direction.

The first axis O1 described above is configured as a passive axis that enables the microscope unit 21 to passively rotate around the first axis O1 by an external force applied from an operator regardless of power of the actuator or the like. Similarly, the fourth to sixth axes O4 to O6 are configured as passive axes. On the other hand, the second axis O2 is configured as an active axis that enables the microscope unit 21 to actively rotate around the second axis O2 by the power of the actuator 236. Similarly, the third axis O3 is configured as an active axis. In FIG. 2, for convenience of explanation, only one of two actuators 236 provided for the second and third axes O2 and O3, respectively, is illustrated.

The state switching unit 234 implemented by an electromagnetic brake or the like and a posture detection unit 235 implemented by a rotary encoder, an angular velocity sensor, or the like are provided in each of the first to sixth joints 232a to 232f. Note that, in FIG. 2, for convenience of explanation, only one of six state switching units 234 provided in the first to sixth joints 232a to 232f is illustrated, and only one of six posture detection units 235 provided in the first to sixth joints 232a to 232f is illustrated.

Under the control of the control device 3, the state switching unit 234 is switched to one of an allowed state in which the rotation of the microscope unit 21 around a corresponding axis (for example, the first axis O1 in a case of the state switching unit 234 provided in the first joint 232a) among the first to sixth axes O1 to O6 is allowed and a restricted state in which the rotation is restricted.

Under the control of the control device 3, the posture detection unit 235 detects a rotation angle of the microscope unit 21 around a corresponding axis (for example, the first axis O1 in a case of the state switching unit 234 provided in the first joint 232a) among the first to sixth axes O1 to O6. That is, the posture detection unit 235 detects a posture of support unit 23. Then, the posture detection unit 235 outputs a signal corresponding to the detected rotation angle to the control device 3.

The light source device 24 is connected to one end of the light guide 25, and supplies illumination light of a light amount designated by the control device 3 to one end of the light guide 25.

The light guide 25 has one end connected to the light source device 24 and the other end connected to the microscope unit 21. Further, the light guide 25 transmits the light supplied from the light source device 24 from one end to the other end, and supplies the light to the microscope unit 21. The light supplied to the microscope unit 21 is emitted from the microscope unit 21 to the observation target. The light (subject image) emitted to the observation target and reflected by the observation target is condensed by the lens unit 2111 in the microscope unit 21 and then captured by the imaging element 2113.

The control device 3 corresponds to the medical image processing device according to the present disclosure. The control device 3 is provided inside the base unit 22 and comprehensively controls the operation of the medical observation system 1. As illustrated in FIG. 2, the control device 3 includes a communication unit 31, an observation image generation unit 32, a control unit 33, and a storage unit 34.

That is, the communication unit 31 corresponds to a captured image acquisition unit according to the present disclosure. The communication unit 31 is an interface that communicates with the microscope unit 21 (communication unit 212), receives the captured image (digital signal) output from the microscope unit 21, and transmits the control signal from the control unit 33.

The observation image generation unit 32 processes the captured image (digital signal) output from the microscope unit 21 and received by the communication unit 31 under the control of the control unit 33. Then, the observation image generation unit 32 generates a video signal for display for displaying the processed captured image, and outputs the video signal to the display device 4. As illustrated in FIG. 2, the observation image generation unit 32 includes an image processor 321 and a display controller 322.

The image processor 321 corresponds to an identification image generation unit and a scaling unit according to the present disclosure. The image processor 321 performs image processing, detection processing, and identification image generation processing on the captured image (digital signal) received by the communication unit 31.

Specifically, examples of the image processing include digital gain processing of multiplying the captured image (digital signal) by a digital gain for amplifying the digital signal, optical black subtraction processing, white balance (WB) adjustment processing, demosaic processing, color matrix subtraction processing, gamma correction processing, YC conversion processing of generating a luminance signal and a color difference signal (Y, Cb/Cr signal), enlargement processing (electronic zoom), and the like.

In addition, the above-described detection processing is processing of performing, based on pixel information (for example, a Y value (luminance signal (Y signal)) of each pixel in a specific detection region in an entire image region of the captured image subjected to the above-described image processing, detection of a contrast or a frequency component of an image in the detection region, detection of an average luminance value or maximum and minimum pixels in the detection region by a filter or the like, comparison with a threshold, and detection of a histogram or the like. In the first embodiment, the detection region is a rectangular region centered on an image center of the captured image. Further, the image processor 321 outputs, to the control device 3, detection information (the contrast, the frequency component, the average luminance value, the maximum and minimum pixels, the histogram, and the like) obtained through the detection processing.

Note that the identification image generation processing will be described in "Operation of Medical Observation System" described later.

The display controller 322 generates the video signal for display for displaying the captured image (the luminance signal and the color difference signal (Y, Cb/Cr signal) subjected to the image processing performed by the image processor 321 or an identification image generated by the identification image generation processing performed by the image processor 321. Further, the display controller 322 outputs the video signal to the display device 4.

The control unit 33 is implemented by a central processing unit (CPU), a field-programmable gate array (FPGA), or the like, and controls the overall operation of the control device 3 in addition to controlling the operations of the microscope unit 21, the light source device 24, and the display device 4.

Specifically, the control unit 33 switches an operation mode of the support unit 23 to a free mode or a fixed mode according to the operation of the brake release switch 215 provided in the microscope unit 21 by the operator.

The free mode is a mode in which all the state switching units 234 provided in the first to sixth joints 232a to 232f are in the allowed state. That is, in the free mode, the operator can rotate the microscope unit 21 around the first to sixth axes O1 to O6 by applying an external force to the support unit 23. The free mode is set for a period in which the operator is pressing the brake release switch 215.

The fixed mode is a mode in which all the state switching units 234 provided in the first to sixth joints 232a to 232f are in the restricted state. That is, in the fixed mode, the operator cannot rotate the microscope unit 21 around the first to sixth axes O1 to O6 even if an external force is applied to the support unit 23. The fixed mode is set for a period in which the operator does not press the brake release switch 215.

In the first embodiment, as the operation mode of the support unit 23, an XY movement operation mode is provided in addition to the free mode and the fixed mode described above.

The XY movement operation mode is an operation mode in which the imaging field of view of the microscope unit 21 is moved in an X-axis direction and a Y-axis direction in accordance with the operation of the foot switch 26 by the operator.

More specifically, in a period in which the operator is operating a lever 261 (FIG. 2) of the foot switch 26 in an X direction, the control unit 33 switches the state switching unit 234 provided in the second joint 232b to the allowed state and operates the actuator 236 provided for the second axis O2. As a result, the microscope unit 21 rotates around the second axis O2. When the operator stops the operation of the lever 261 in the X direction, the control unit 33 stops the operation of the actuator 236 and switches the state switching unit 234 to the restricted state.

On the other hand, in a period in which the operator is operating the lever 261 of the foot switch 26 in a Y direction, the control unit 33 switches the state switching unit 234 provided in the third joint 232c to the allowed state and operates the actuator 236 provided for the third axis O3. As a result, the microscope unit 21 rotates around the third axis O3. When the operator stops the operation of the lever 261 in the Y direction, the control unit 33 stops the operation of the actuator 236 and switches the state switching unit 234 to the restricted state.

Furthermore, the control unit 33 calculates an evaluation value based on the detection information obtained by the detection processing performed by the image processor 321.

Specifically, the control unit 33 calculates, based on the detection information (the contrast or frequency component), a focusing evaluation value for evaluating a focusing state of an image in the detection region in the entire image region of the captured image. For example, the control unit 33 uses, as the focusing evaluation value, the contrast obtained by the detection processing performed by the image processor 321 or the sum of high frequency components among frequency components obtained by the detection processing. Note that the larger the focusing evaluation value, the more accurate the focusing is.

Further, the control unit 33 calculates, based on the detection information (average luminance value), a brightness evaluation value for changing a brightness of the image in the detection region in the entire image region of the captured image to a reference brightness (changing the detection information (average luminance value) to a reference average luminance value). As the brightness evaluation value, the following first to fourth brightness evaluation values can be exemplified.

The first brightness evaluation value is an exposure time of each pixel in the imaging element 2113.

The second brightness evaluation value is an analog gain multiplied by the signal processor 2114.

The third brightness evaluation value is a digital gain multiplied by the image processor 321.

The fourth brightness evaluation value is the amount of light supplied by the light source device 24.

Furthermore, the control unit 33 performs AF processing for adjusting the focal position of the lens unit 2111.

Specifically, the control unit 33 controls the operation of the driving unit 213 by a hill-climbing method or the like based on the calculated focusing evaluation value and the current focal position detected by the detection unit 214, thereby performing the AF processing of positioning the focus lens 2111a at the focal position where the image in the detection region in the entire image region of the captured image is in focus.

In addition, the control unit 33 performs brightness adjustment processing of adjusting the brightness of the image in the detection region of the entire image region of the captured image to the reference brightness.

Specifically, in a case where the calculated brightness evaluation value is the first brightness evaluation value, the control unit 33 outputs the control signal to the microscope unit 21, and sets the exposure time of each pixel of the imaging element 2113 as the first brightness evaluation value. Furthermore, in a case where the calculated brightness evaluation value is the second brightness evaluation value, the control unit 33 outputs the control signal to the microscope unit 21, and sets the analog gain multiplied by the signal processor 2114 as the second brightness evaluation value. Furthermore, in a case where the calculated brightness evaluation value is the third brightness evaluation value, the control unit 33 outputs the control signal to the image processor 321, and sets the digital gain multiplied by the image processor 321 as the third brightness evaluation value. Furthermore, in a case where the calculated brightness evaluation value is the fourth brightness evaluation value, the control unit 33 outputs the control signal to the light source device 24, and sets the amount of light supplied by the light source device 24 as the fourth brightness evaluation value.

Furthermore, the control unit 33 corresponds to a determination unit according to the present disclosure. Note that the function (determination processing) of the determination unit will be described in "Operation of Medical Observation System" described later.

The storage unit 34 stores a program to be executed by the control unit 33, information necessary for processing performed by the control unit 33, and the like.

The display device 4 is implemented by a display using liquid crystal, organic electro luminescence (EL), or the like, and displays the captured image, the identification image, or the like based on the video signal from the display controller 322.

[Operation of Medical Observation System]

Next, the operation of the medical observation system 1 will be described.

Figure 3:
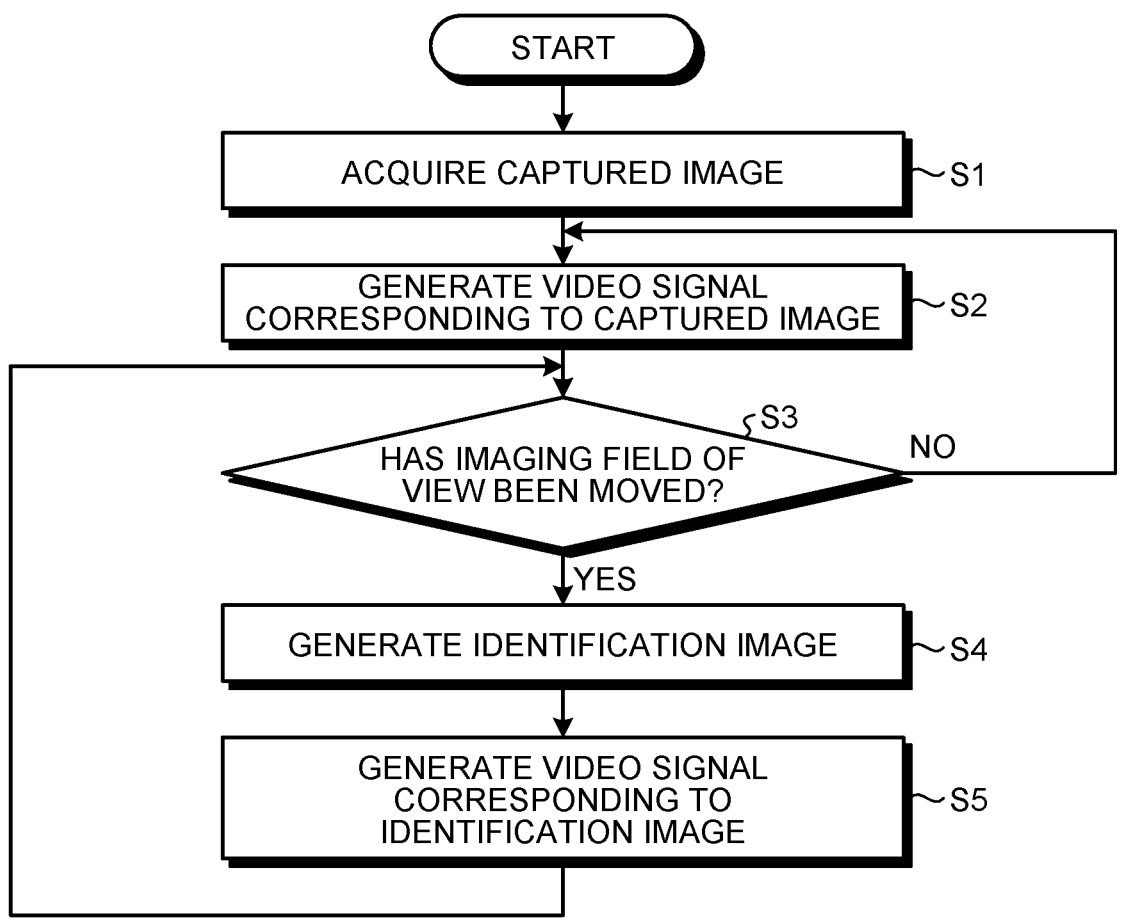
FIG. 3 is a flowchart illustrating an operation of the medical observation system.
Figure 4:
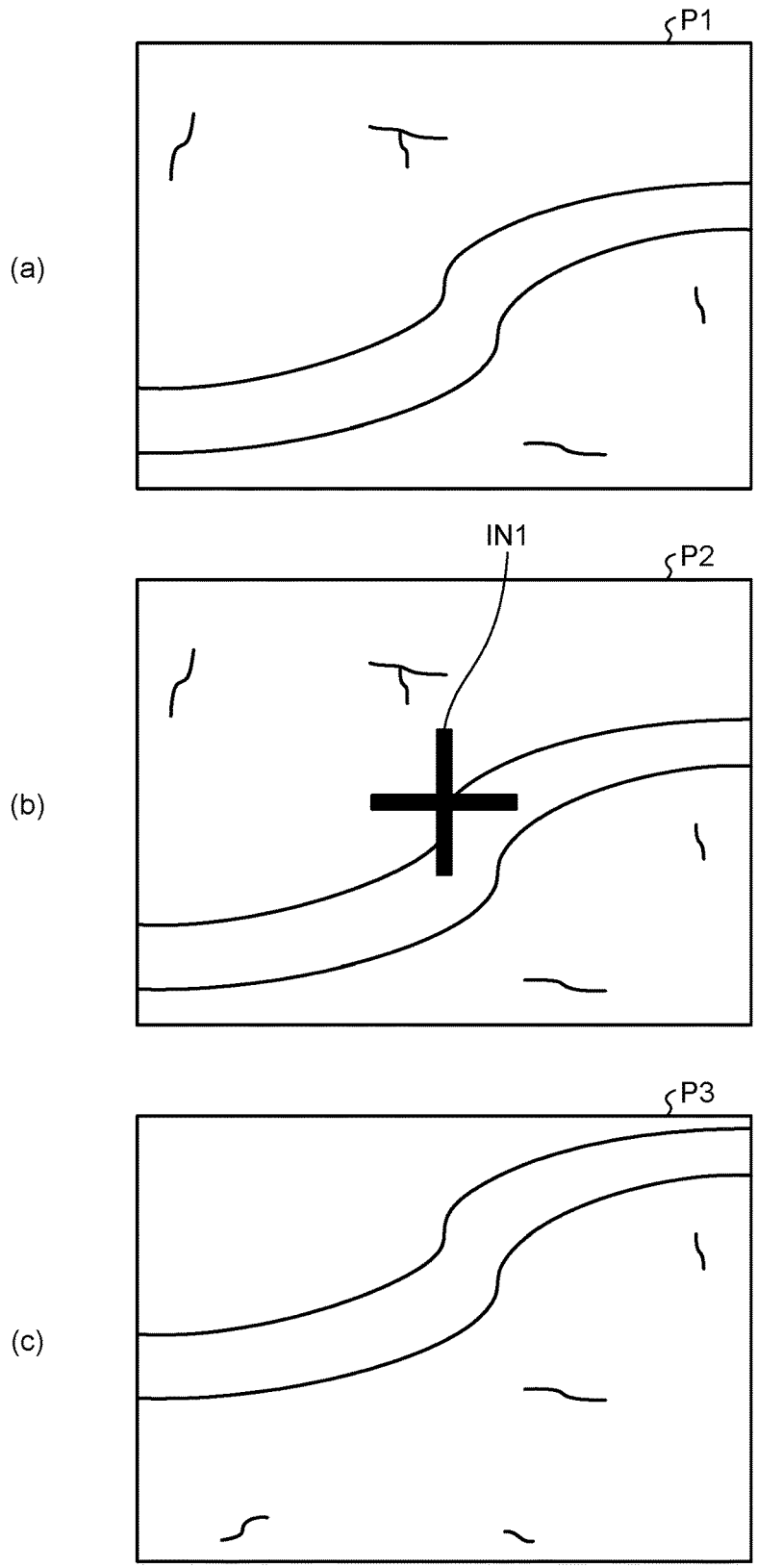
FIG. 4 is a view for describing the operation of the medical observation system.

FIG. 3 is a flowchart illustrating the operation of the medical observation system 1. FIG. 4 is a diagram for describing the operation of the medical observation system 1.

First, the control unit 33 drives the light source device 24. As a result, the observation target is irradiated with the light emitted from the light source device 24 by the microscope unit 21. Furthermore, the control unit 33 causes the imaging element 2113 to capture the subject image emitted to the observation target and reflected by the observation target at a predetermined frame rate. Then, the microscope unit 21 sequentially generates the captured images by capturing the subject image. As a result, the communication unit 31 sequentially receives the captured images from the microscope unit 21 (Step S1).

After Step S1, the image processor 321 performs the image processing on the captured image received in Step S1. Furthermore, the display controller 322 generates the video signal for display corresponding to the captured image subjected to the image processing (Step S2). Then, the display device 4 displays the captured image corresponding to the video signal.

After Step S2, the control unit 33 performs the determination processing (Step S3).

Specifically, in Step S3, the control unit 33 performs the determination processing of determining whether or not the imaging field of view of the microscope unit 21 has been moved. In the first embodiment, the control unit 33 determines that the imaging field of view of the microscope unit 21 has been moved in a case where the rotation angle per unit time of the microscope unit 21 detected by at least one of the posture detection units 235 provided in the first to sixth joints 232a to 232f is larger than 0 and equal to or smaller than a specific threshold. On the other hand, in a case where the rotation angle per unit time of the microscope unit 21 exceeds the specific threshold, the control unit 33 determines that the imaging field of view of the microscope unit 21 has not been moved.

In a case where it is determined in the determination processing that the imaging field of view of the microscope unit 21 has not been moved (Step S3: No), the control device 3 returns to Step S2.

On the other hand, in a case where it is determined in the determination processing that the imaging field of view of the microscope unit 21 has been moved (Step S3: Yes), the image processor 321 performs the identification image generation processing (Step S4).

Specifically, in Step S4, the image processor 321 performs the identification image generation processing of generating the identification image in which a specific position in a specific region displayed on the display device 4 in the entire image region of the captured image subjected to the image processing is identifiable with respect to other positions.

Here, the enlargement processing (electronic zoom) performed by the image processor 321 is processing of cutting out, for example, a rectangular region centered on the image center in the entire image region of the captured image from the captured image, and enlarging an image of the rectangular region at a designated zoom magnification. In the first embodiment, in a case where the designated zoom magnification is one time, the entire image region of the captured image is set as the rectangular region. Note that even in a case where the designated zoom magnification is one time, a partial region of the entire image region of the captured image may be set as the rectangular region. Further, the specific region is the rectangular region cut out in the enlargement processing (electronic zoom). Further, the specific position is a center position of the specific region. In addition, the identification image is, for example, an identification image P2 in which an index IN1 indicating an image center of a captured image P1 (the entire image region is the specific region) is superimposed on the image center of the captured image P1 as illustrated in FIG. 4(*b*). The index IN1 has a black cross shape.

After Step S4, the display controller 322 generates the video signal for display corresponding to the identification image generated by the identification image generation processing in Step S4 (Step S5). Then, the display device 4 displays the identification image corresponding to the video signal.

After Step S5, the control device 3 returns to Step S3.

With the above operation, the image illustrated in FIG. 4 is displayed on the display device 4.

That is, in a period before the movement of the imaging field of view of the microscope unit 21 is started, the captured image P1 (FIG. 4(*a*)) based on the video signal generated in Step S2 is displayed on the display device 4.

In addition, in a period in which the imaging field of view of the microscope unit 21 is moving (in a case where it is determined in Step S3 that the imaging field of view of the microscope unit 21 has been moved), the identification image P2 (FIG. 4(*b*)) based on the video signal generated in Step S5 is displayed on the display device 4.

Then, in a period after the movement of the imaging field of view of the microscope unit 21 ends, a captured image P3 (FIG. 4(*c*)) based on the video signal generated in Step S2 is displayed on the display device 4.

According to the first embodiment described above, the following effects are obtained.

In a case where it is determined that the imaging field of view in the medical observation device 2 (microscope unit 21) has been moved, the control device 3 according to the first embodiment generates the identification image in which the index IN1 is applied to the image center (specific position) of the captured image (the entire image region is the specific region).

Therefore, the observer can clearly determine the image center of the captured image by the index IN1, and can easily position a part to be observed at the image center by moving the imaging field of view of the microscope unit 21. In addition, in a case where the imaging field of view of the microscope unit 21 has not move, the index IN1 is deleted, and thus, the index IN1 does not become an obstacle at the time of observation.

Therefore, the control device 3 according to the first embodiment can improve convenience.

Positioning the part to be observed at the image center of the captured image by the index IN1 is particularly important when fine adjustment of the imaging field of view of the microscope unit 21 is performed.

The control device 3 according to the first embodiment determines that the imaging field of view of the microscope unit 21 has been moved in a case where the rotation angle per unit time of the microscope unit 21 detected by at least one of the posture detection units 235 provided in the first to sixth joints 232*a* to 232*f* is larger than 0 and equal to or smaller than the specific threshold. That is, the index IN1 is not displayed when performing coarse adjustment in which the imaging field of view of the microscope unit 21 is largely moved, and the index IN1 is displayed only when performing fine adjustment. Therefore, the index IN1 can be displayed only when the index IN1 is necessary.

Second Embodiment

Next, a second embodiment will be described.

In the following description, the same components as those in the first embodiment will be designated by the same reference signs, and a detailed description thereof will be omitted or simplified.

Figure 5:
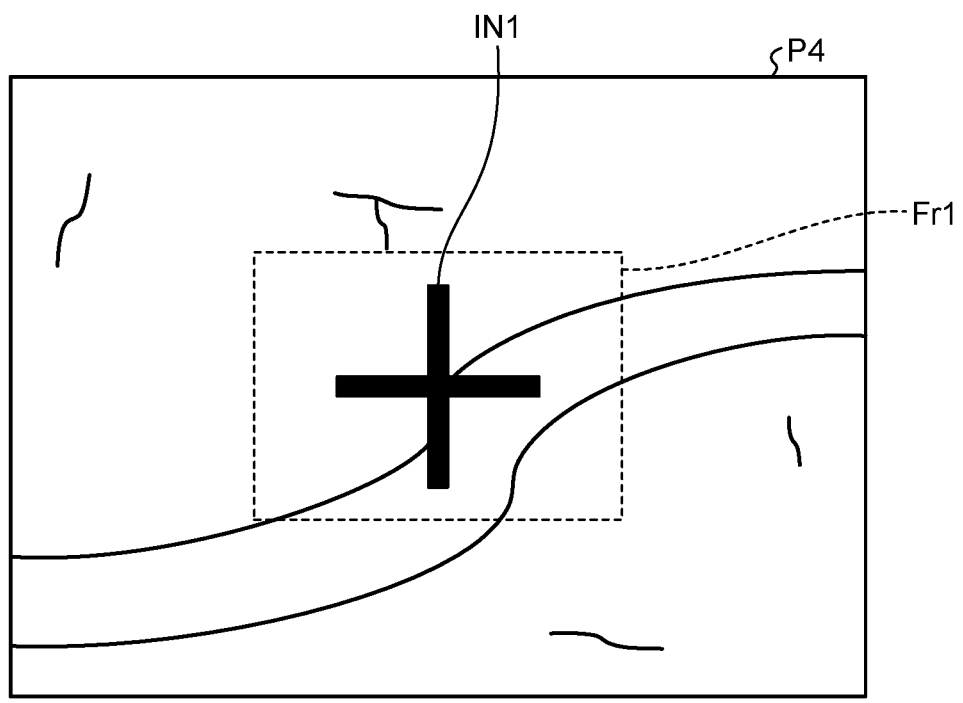
FIG. 5 is a view illustrating an identification image according to a second embodiment.

FIG. 5 is a diagram illustrating an identification image P4 according to the second embodiment.

In the second embodiment, an identification image (for example, the identification image P4 illustrated in FIG. 5) different from that of the above-described first embodiment is generated in the identification image generation processing (Step S4).

In the second embodiment, the identification image P4 generated by the image processor 321 in the identification image generation processing is as follows.

As illustrated in FIG. 5, the identification image P4 is an image in which the index IN1 indicating the image center of the captured image (the entire image region is the specific region) subjected to the image processing is superimposed on the image center (specific position), and a detection frame Fr1 indicating the detection region used in the detection processing is further superimposed. Note that the detection frame Fr1 does not necessarily coincide with the detection region. The detection frame Fr1 may be a frame smaller or larger than the detection region. In other words, the detection frame Fr1 may be superimposed as a frame corresponding to the detection region.

According to the second embodiment described above, in addition to the same effect as that of the first embodiment described above, the following effects are obtained.

In a case where the imaging field of view of the microscope unit 21 is moving, the control device 3 according to the second embodiment generates the identification image in which the detection frame Fr1 indicating the detection region used in the detection processing is added in addition to the index IN1.

Therefore, if the observer moves the imaging field of view of the microscope unit 21 and positions the part to be observed inside the detection frame Fr1, the part can be in focus and have an appropriate brightness. Therefore, convenience can be further improved.

Third Embodiment

Next, a third embodiment will be described.

In the following description, the same components as those in the first embodiment will be designated by the same reference signs, and a detailed description thereof will be omitted or simplified.

Figure 6:
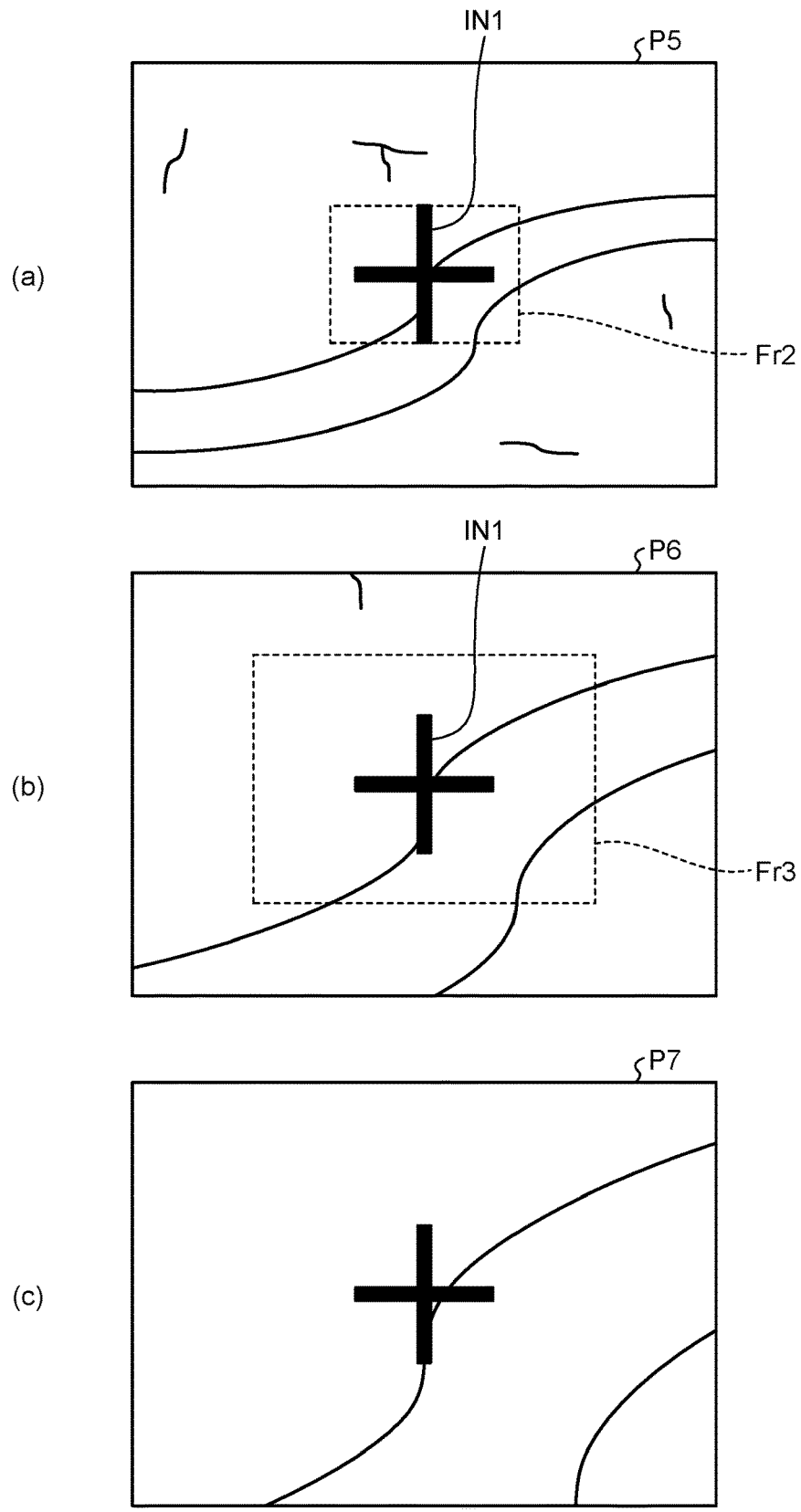
FIG. 6 is a view illustrating an identification image according to a third embodiment.

FIG. 6 is a diagram illustrating identification images P5 to P7 according to the third embodiment.

In the third embodiment, identification images (for example, the identification images P5 and P6 illustrated in FIGS. 6(a) and 6(b)) different from that of the above-described first embodiment are generated in the identification image generation processing (Step S4).

In the third embodiment, the identification images P5 to P7 generated by the image processor 321 in the identification image generation processing are as follows.

For example, it is assumed that the designated zoom magnification is a low zoom magnification (corresponding to a first zoom magnification according to the present disclosure) in the enlargement processing (electronic zoom) performed by the image processor 321. In this case, the image processor 321 generates the identification image P5 illustrated in FIG. 6(a) in the identification image generation processing.

Specifically, as illustrated in FIG. 6(a), the identification image P5 is an image in which the index IN1 indicating the image center (specific position) of the captured image (the entire image region is the specific region) subjected to the image processing (including the above-described enlargement processing (electronic zoom) at the low zoom magnification) is superimposed on the image center, and an observation frame Fr2 indicating an observation range (corresponding to the entire image region of the identification image P7 illustrated in FIG. 6(c)) in a case where the enlargement processing (electronic zoom) is performed at a high zoom magnification (corresponding to a second zoom magnification according to the present disclosure) higher than the low zoom magnification is superimposed.

Further, it is assumed that the designated zoom magnification is a medium zoom magnification (corresponding to the first zoom magnification according to the present disclosure) in the enlargement processing (electronic zoom) performed by the image processor 321. In this case, the image processor 321 generates the identification image P6 illustrated in FIG. 6(b) in the identification image generation processing.

Specifically, as illustrated in FIG. 6(b), the identification image P6 is an image in which the index IN1 indicating the image center (specific position) of the captured image (the entire image region is the specific region) subjected to the image processing (including the above-described enlargement processing (electronic zoom) at the medium zoom magnification) is superimposed on the image center, and an observation frame Fr3 indicating an observation range (corresponding to the entire image region of the identification image P7 illustrated in FIG. 6(c)) in a case where the enlargement processing (electronic zoom) is performed at a high zoom magnification (corresponding to the second zoom magnification according to the present disclosure) higher than the medium zoom magnification is superimposed.

Further, it is assumed that the designated zoom magnification is a high zoom magnification (corresponding to the second zoom magnification according to the present disclosure) in the enlargement processing (electronic zoom) performed by the image processor 321. In this case, the image processor 321 generates the identification image P7 illustrated in FIG. 6(c) in the identification image generation processing.

Specifically, as illustrated in FIG. 6(c), the identification image P7 is an image in which only the index IN1 indicating the image center (specific position) of the captured image (the entire image region is the specific region) subjected to the image processing (including the above-described enlargement processing (electronic zoom) at the high zoom magnification) is superimposed on the image center.

According to the third embodiment described above, in addition to the same effect as that of the first embodiment described above, the following effects are obtained.

In a case where the imaging field of view of the microscope unit 21 is moving, the control device 3 according to the third embodiment generates the identification image in which the observation frames Fr2 and Fr3 indicating the observation ranges in a case where the enlargement processing (electronic zoom) is performed at the high zoom magnification are added in addition to the index IN1.

Therefore, if the observer moves the imaging field of view of the microscope unit 21 and positions the part to be observed in the observation frames Fr2 and Fr3, it is possible to avoid a situation in which at least a portion of the part to be observed is not displayed when the zoom magnification is switched to a high magnification.

Fourth Embodiment

Next, a fourth embodiment will be described.

In the following description, the same components as those in the first embodiment will be designated by the same reference signs, and a detailed description thereof will be omitted or simplified.

Figure 7:
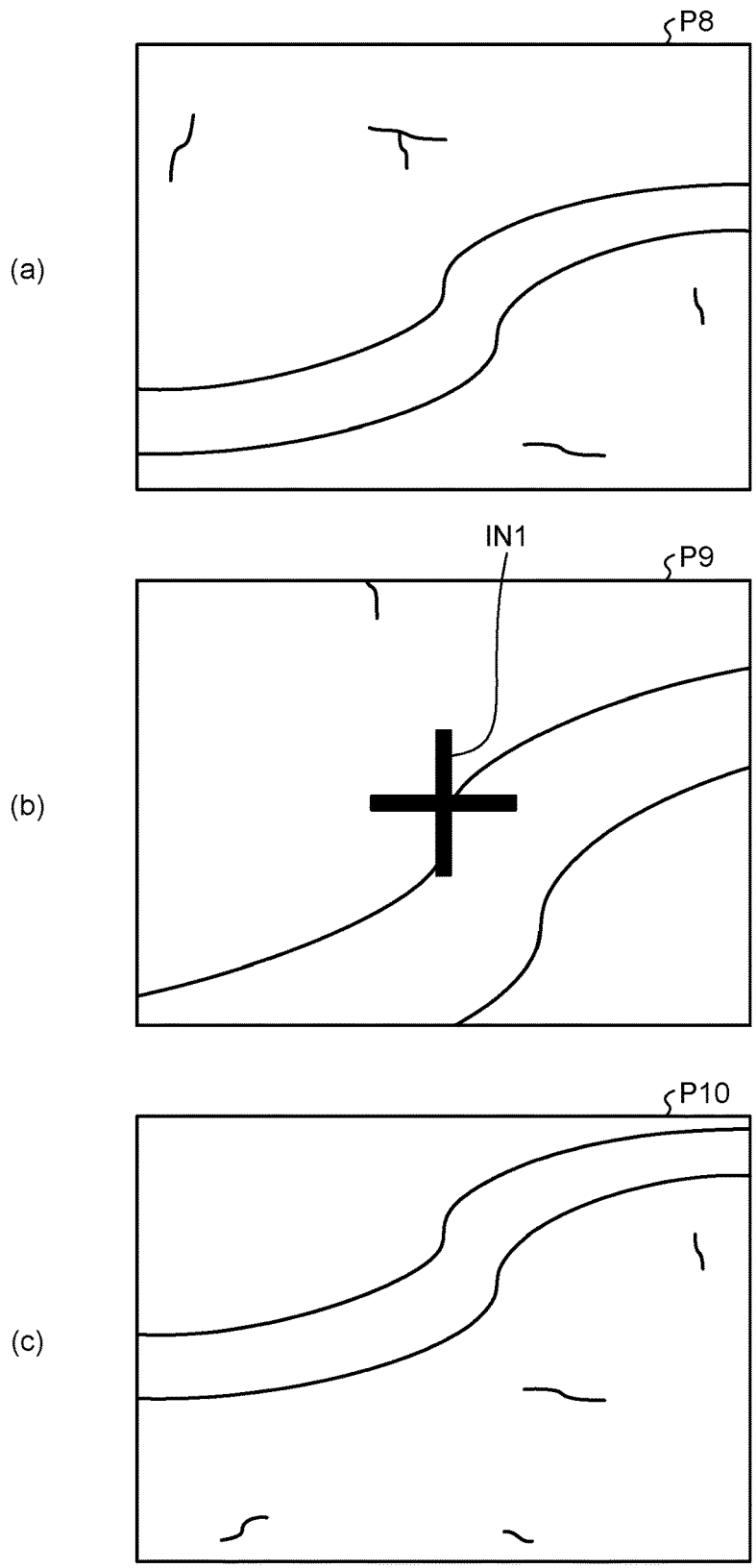
FIG. 7 is a view illustrating an identification image according to a fourth embodiment.

FIG. 7 is a diagram illustrating an identification image P9 according to the fourth embodiment.

In the fourth embodiment, an identification image (for example, the identification image P9 illustrated in FIG. 7(b)) different from that of the above-described first embodiment is generated in the identification image generation processing (Step S4).

Here, it is assumed that the designated zoom magnification is a low zoom magnification (corresponding to the first zoom magnification according to the present disclosure) in the enlargement processing (electronic zoom) performed by the image processor 321.

In this case, the image processor 321 performs the enlargement processing (electronic zoom) at the low zoom magnification in a period before the movement of the imaging field of view of the microscope unit 21 is started. Then, a captured image P8 (FIG. 7(a)) is generated by the image processing (including the enlargement processing (electronic zoom) at the low zoom magnification) performed by the image processor 321. Note that the image processor 321 does not perform the identification image generation processing in the period in which the imaging field of view of the microscope unit 21 has not been moved.

Furthermore, the image processor 321 performs switching to a zoom magnification (corresponding to the second zoom magnification according to the present disclosure) higher than the low zoom magnification in a period in which the imaging field of view of the microscope unit 21 is moving, and performs the enlargement processing (electronic zoom) at the high zoom magnification. Further, the image processor 321 performs the identification image generation processing and generates the identification image P9 illustrated in FIG. 7(b).

Specifically, as illustrated in FIG. 7(b), the identification image P9 is an image in which the index IN1 indicating the image center (specific position) of the captured image (the entire image region is the specific region) subjected to the image processing (including the above-described enlargement processing (electronic zoom) at the high zoom magnification) is superimposed on the image center.

Then, in a period after the movement of the imaging field of view of the microscope unit 21 ends, the image processor 321 switches the above-described high zoom magnification to the original low zoom magnification, and performs the enlargement processing (electronic zoom) at the low zoom magnification. Then, a captured image P10 (FIG. 7(c)) is generated by the image processing (including the enlargement processing (electronic zoom) at the low zoom magnification) performed by the image processor 321. Note that the image processor 321 does not perform the identification image generation processing in the period in which the imaging field of view of the microscope unit 21 has not been moved.

According to the fourth embodiment described above, in addition to the same effect as that of the first embodiment described above, the following effects are obtained.

The control device 3 according to the fourth embodiment switches the zoom magnification to a high zoom magnification in a period in which the imaging field of view of the microscope unit 21 is moving, and generates the identification image P9 corresponding to the high zoom magnification.

Therefore, even in a case where the designated zoom magnification is a low zoom magnification, the observer can move the imaging field of view of the microscope unit 21 while checking the identification image P9 with the high zoom magnification, and can easily position the part to be observed at the image center (index IN1) of the identification image P9.

Fifth Embodiment

Next, a fifth embodiment will be described.

In the following description, the same components as those in the first embodiment will be designated by the same reference signs, and a detailed description thereof will be omitted or simplified.

FIG. 8 is a diagram illustrating an identification image P12 according to the fifth embodiment.

In the fifth embodiment, an identification image (for example, the identification image P12 illustrated in FIG. 8(*b*)) different from that of the above-described first embodiment is generated in the identification image generation processing (Step S4).

Here, it is assumed that the designated zoom magnification is a high zoom magnification (corresponding to the second zoom magnification according to the present disclosure) in the enlargement processing (electronic zoom) performed by the image processor 321.

In this case, the image processor 321 performs the enlargement processing (electronic zoom) at the high zoom magnification in a period before the movement of the imaging field of view of the microscope unit 21 is started. Then, a captured image P11 (FIG. 8(*a*)) is generated by the image processing (including the enlargement processing (electronic zoom) at the high zoom magnification) performed by the image processor 321. Note that the image processor 321 does not perform the identification image generation processing in the period in which the imaging field of view of the microscope unit 21 has not been moved.

Furthermore, the image processor 321 performs switching to a zoom magnification (corresponding to the first zoom magnification according to the present disclosure) lower than the high zoom magnification in a period in which the imaging field of view of the microscope unit 21 is moving, and performs the enlargement processing (electronic zoom) at the low zoom magnification. Further, the image processor 321 performs the identification image generation processing and generates the identification image P12 illustrated in FIG. 8(*b*).

Specifically, as illustrated in FIG. 8(*b*), the identification image P12 is an image in which the index IN1 indicating the image center (specific position) of the captured image (the entire image region is the specific region) subjected to the image processing (including the above-described enlargement processing (electronic zoom) at the low zoom magnification) is superimposed on the image center.

Then, in a period after the movement of the imaging field of view of the microscope unit 21 ends, the image processor 321 switches the above-described low zoom magnification to the original high zoom magnification, and performs the enlargement processing (electronic zoom) at the high zoom magnification. Then, a captured image P13 (FIG. 8(*c*)) is generated by the image processing (including the enlargement processing (electronic zoom) at the high zoom magnification) performed by the image processor 321. Note that the image processor 321 does not perform the identification image generation processing in the period in which the imaging field of view of the microscope unit 21 has not been moved.

According to the fifth embodiment described above, in addition to the same effect as that of the first embodiment described above, the following effects are obtained.

By the way, in a case where the imaging field of view of the microscope unit 21 is moved while checking the captured image with a high zoom magnification, there is a possibility that the observer loses sight of the part to be observed.

The control device 3 according to the fifth embodiment switches the zoom magnification to a low zoom magnification in a period in which the imaging field of view of the microscope unit 21 is moving, and generates the identification image P12 corresponding to the low zoom magnification.

Therefore, even in a case where the designated zoom magnification is a high zoom magnification, the observer moves the imaging field of view of the microscope unit 21 while checking the identification image P12 with a low zoom magnification, and thus, there is no possibility that the observer loses sight of the part to be observed.

Sixth Embodiment

Next, a sixth embodiment will be described.

In the following description, the same components as those in the first embodiment will be designated by the same reference signs, and a detailed description thereof will be omitted or simplified.

Figure 9:
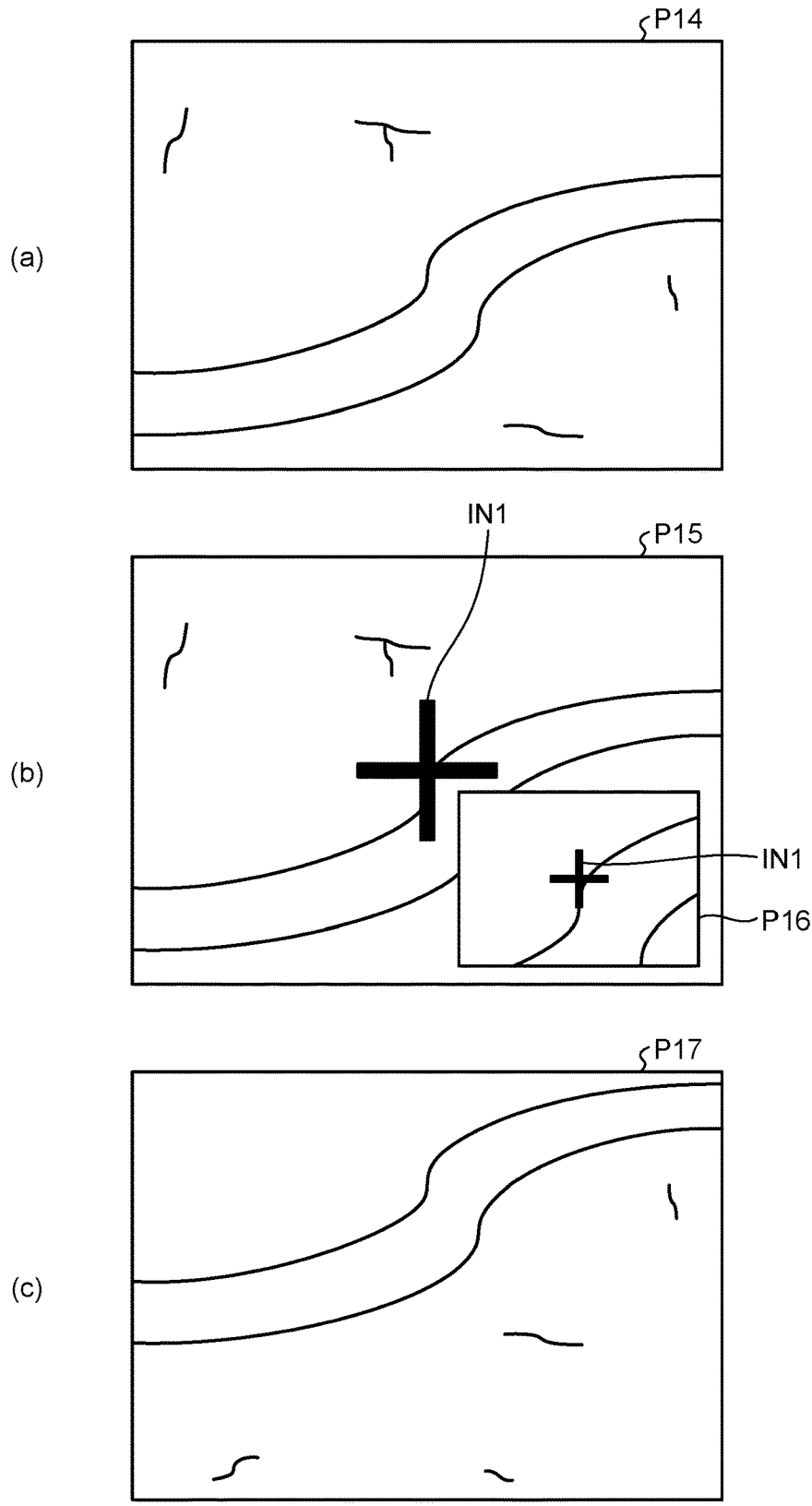
FIG. 9 is a view illustrating an identification image according to a sixth embodiment.

FIG. 9 is a diagram illustrating identification images P15 and P16 according to the sixth embodiment.

In the sixth embodiment, an identification image (for example, the identification images P15 and P16 illustrated in FIG. 9(*b*)) different from that of the above-described first embodiment is generated in the identification image generation processing (Step S4).

Here, it is assumed that the designated zoom magnification is a low zoom magnification (corresponding to the first zoom magnification according to the present disclosure) in the enlargement processing (electronic zoom) performed by the image processor 321.

In this case, the image processor 321 performs the enlargement processing (electronic zoom) at the low zoom magnification in a period before the movement of the imaging field of view of the microscope unit 21 is started. Then, a captured image P14 (FIG. 9(*a*)) is generated by the image processing (including the enlargement processing (electronic zoom) at the low zoom magnification) performed by the image processor 321. Note that the image processor 321 does not perform the identification image generation processing in the period in which the imaging field of view of the microscope unit 21 has not been moved.

Furthermore, in a period in which the imaging field of view of the microscope unit 21 is moving, the image processor 321 simultaneously performs the enlargement processing (electronic zoom) at a low zoom magnification and the enlargement processing (electronic zoom) at a zoom magnification (corresponding to the second zoom magnification according to the present disclosure) higher than the low zoom magnification. Further, the image processor 321 performs the identification image generation processing and generates the identification images P15 and P16 illustrated in FIG. 9(*b*).

Specifically, the identification image P15 corresponds to a first identification image according to the present disclosure. As illustrated in FIG. 9(*b*), the identification image P15 is an image in which the index IN1 indicating the image center (specific position) of the captured image (the entire image region is the specific region) subjected to the image processing (including the above-described enlargement processing (electronic zoom) at the low zoom magnification) is superimposed on the image center.

In addition, the identification image P16 corresponds to a second identification image according to the present disclosure. As illustrated in FIG. 9(*b*), the identification image P16 is an image in which the index IN1 indicating the image center (specific position) of the captured image (the entire image region is the specific region) subjected to the image processing (including the above-described enlargement processing (electronic zoom) at the high zoom magnification) is superimposed on the image center.

Then, as illustrated in FIG. 9(*b*), the identification image P16 is displayed on the display device 4 as a child image in a picture-in-picture mode together with the identification image P15.

Note that, in the above description, a case where the designated zoom magnification is a low zoom magnification in the enlargement processing (electronic zoom) performed by the image processor 321 has been assumed, but the present disclosure is not limited thereto. For example, even in a case where the designated zoom magnification is the high zoom magnification described above, the above-described identification images P15 and P16 may be generated. In this case, the identification image P15 is displayed on the display device 4 as a child image in the picture-in-picture mode together with the identification image P16.

Then, the image processor 321 performs the enlargement processing (electronic zoom) only at the original low zoom magnification in a period after the movement of the imaging field of view of the microscope unit 21 ends. Then, a captured image P17 (FIG. 9(*c*)) is generated by the image processing (including the enlargement processing (electronic zoom) at the low zoom magnification) performed by the image processor 321. Note that the image processor 321 does not perform the identification image generation processing in the period in which the imaging field of view of the microscope unit 21 has not been moved.

According to the sixth embodiment described above, the same effects as those of the first, fourth, and fifth embodiments described above are obtained.

Seventh Embodiment

Next, a seventh embodiment will be described.

In the following description, the same components as those in the first embodiment will be designated by the same reference signs, and a detailed description thereof will be omitted or simplified.

Figure 10:
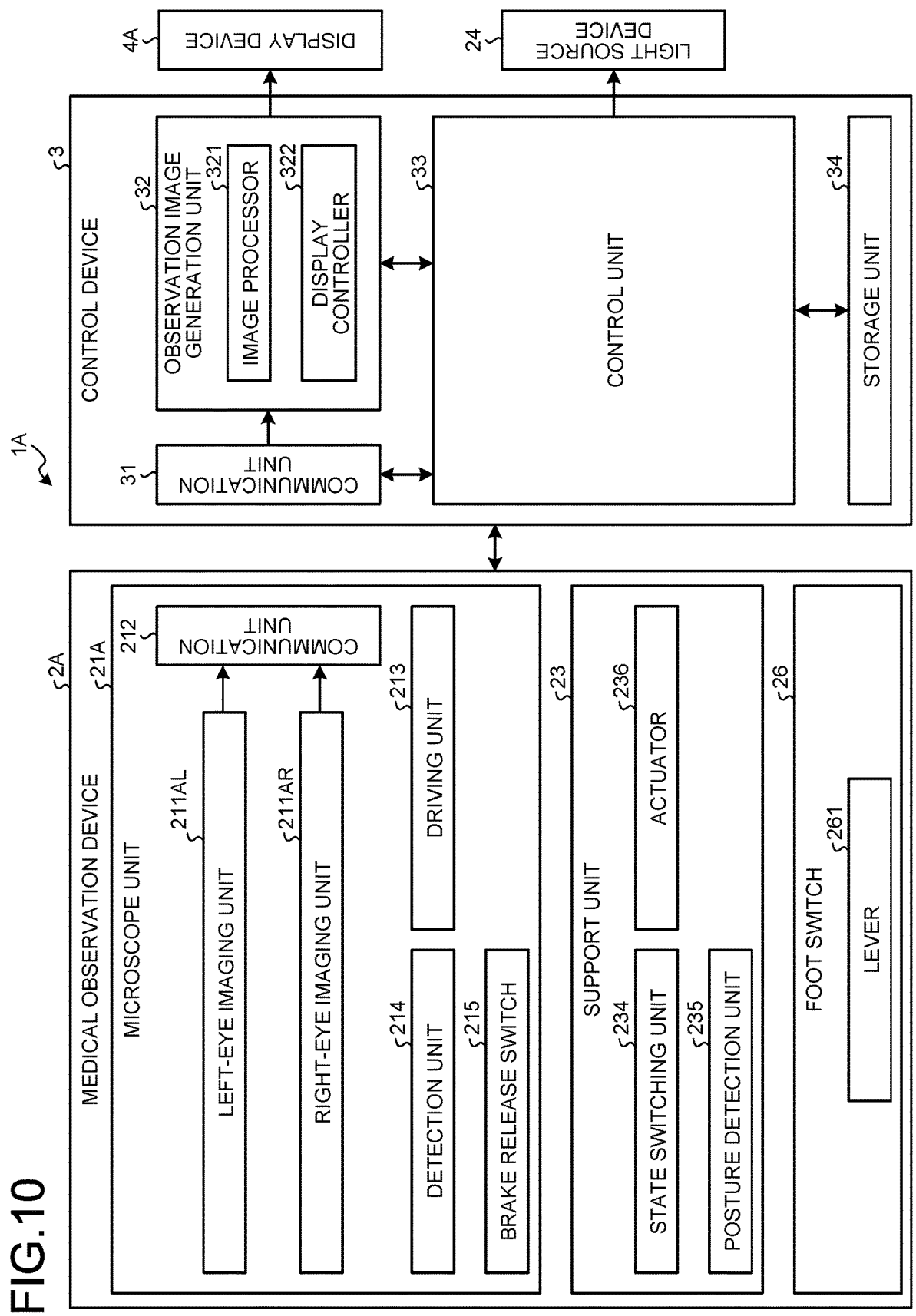
FIG. 10 is a block diagram illustrating a medical observation system according to a seventh embodiment.

FIG. 10 is a block diagram illustrating a medical observation system 1A according to the seventh embodiment.

The medical observation system 1A according to the seventh embodiment is configured as a system that three-dimensionally displays a captured image.

Specifically, a display device 4A included in the medical observation system 1A is implemented by an active or passive 3D display.

In addition, a medical observation device 2A (microscope unit 21A) included in the medical observation system 1A functions as a stereo camera. That is, the microscope unit 21A includes a left-eye imaging unit 211AL and a right-eye imaging unit 211AR instead of the imaging unit 211 described in the above-described first embodiment. Although configurations of the left-eye imaging unit 211AL and the right-eye imaging unit 211AR are not illustrated, the configurations are similar to that of the imaging unit 211. Further, the left-eye imaging unit 211AL and the right-eye imaging unit 211AR respectively generate a left-eye captured image and a right-eye captured image having a parallax with each other.

For convenience of explanation, only one driving unit 213 is illustrated in FIG. 10, but the driving unit 213 is provided for each of the left-eye imaging unit 211AL and the right-eye imaging unit 211AR. The same applies to the detection unit 214.

In the seventh embodiment, the image processor 321 performs the image processing, the detection processing, and the identification image generation processing (only in a period in which the imaging field of view of the microscope unit 21A is moving) described in the above-described first embodiment on the left-eye captured image and the right-eye captured image received from the microscope unit 21A via the communication unit 31.

The identification image generation processing according to the seventh embodiment will be described below.

The image processor 321 calculates a depth position (image depth) of an image center (specific position) of each of the left-eye captured image (the entire image region is the specific region) and the right-eye captured image (the entire image region is the specific region) by a known method (see, for example, JP 2019-154886 A). Further, the image processor 321 generates a left-eye identification image in which an index indicating the image center of the left-eye captured image subjected to the image processing is added to the image center in such a way as to correspond to the depth position. In addition, the image processor 321 generates a right-eye identification image in which an index indicating the image center of the right-eye captured image subjected to the image processing is added to the image center in such a way as to correspond to the depth position.

Further, in the seventh embodiment, the display controller 322 generates a three-dimensional video signal such as a side-by-side method from the left-eye identification image and the right-eye identification image, and outputs the three-dimensional video signal to the display device 4A. As a result, the display device 4A three-dimensionally displays the left-eye identification image and the right-eye identification image based on the three-dimensional video signal.

In a period in which the imaging field of view of the microscope unit 21A is not moving, the display controller 322 generates the three-dimensional video signal from the left-eye captured image and right-eye captured image subjected to the image processing and outputs the three-dimensional video signal to the display device 4A. As a result, the display device 4A three-dimensionally displays the left-eye captured image and the right-eye captured image based on the three-dimensional video signal.

According to the seventh embodiment described above, in addition to the same effect as that of the first embodiment described above, the following effects are obtained.

The control device 3 according to the seventh embodiment calculates the depth position of the image center of each of the left-eye captured image and the right-eye captured image in a period in which the imaging field of view of the microscope unit 21A is moving. Then, the control device 3 generates the left-eye identification image in which the index indicating the image center of the left-eye captured image is added to the image center in such a way as to correspond to the depth position, and the right-eye identification image in which the index indicating the image center of the right-eye captured image is added to the image center in such a way as to correspond to the depth position.

Therefore, the observer can move the imaging field of view of the microscope unit 21A and position a part to be observed on the index (image center) without giving a sense of discomfort in depth feeling of the index.

Eighth Embodiment

Next, an eighth embodiment will be described.

In the following description, the same components as those in the first embodiment will be designated by the same reference signs, and a detailed description thereof will be omitted or simplified.

In the eighth embodiment, the control unit 33 performs determination processing (Step S3) different from that in the first embodiment described above.

Specifically, the control unit 33 determines that the imaging field of view of the microscope unit 21 has been moved in a period in which the operator is pressing the brake release switch 215 or in a period in which the operator is operating the lever 261. On the other hand, the control unit 33 determines that the imaging field of view of the microscope unit 21 has not been moved in a period in which the operator does not press the brake release switch 215 and does not operate the lever 261. That is, the brake release switch 215 and the lever 261 correspond to an operating unit according to the present disclosure.

According to the eighth embodiment described above, in addition to the same effect as that of the first embodiment described above, the following effects are obtained.

The control device 3 according to the eighth embodiment performs the above-described determination processing. Therefore, a processing load of the determination processing can be reduced.

Ninth Embodiment

Next, a ninth embodiment will be described.

In the following description, the same components as those in the first embodiment will be designated by the same reference signs, and a detailed description thereof will be omitted or simplified.

In the first embodiment described above, the present disclosure is applied to the medical observation system 1 using a surgical microscope (medical observation device 2).

On the other hand, in the ninth embodiment, the present disclosure is applied to a medical observation system using a rigid endoscope.

Figure 11:
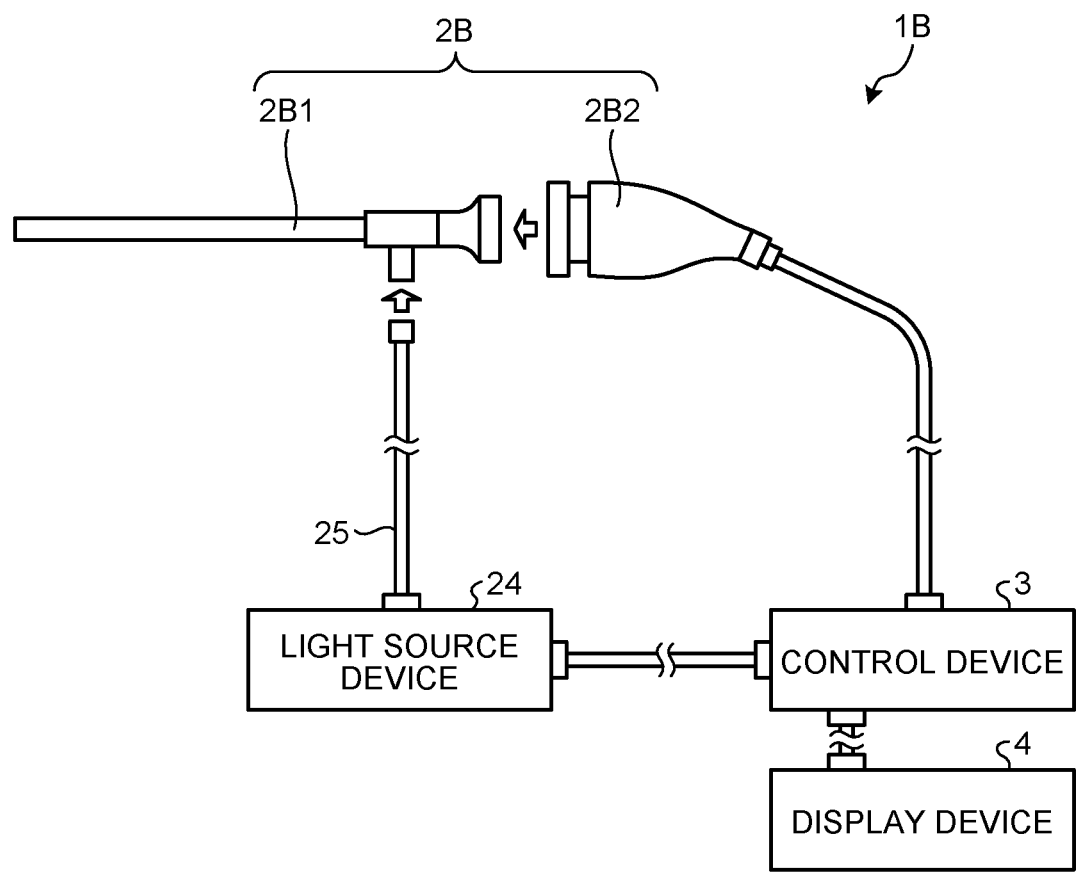
FIG. 11 is a view illustrating a medical observation system according to a ninth embodiment.

FIG. 11 is a diagram illustrating a medical observation system 1B according to the ninth embodiment.

As illustrated in FIG. 11, the medical observation system 1B according to the ninth embodiment includes a rigid endoscope 2B, a light source device 24 that is connected to the rigid endoscope 2B via a light guide 25 and generates illumination light emitted from a distal end of the rigid endoscope 2B, a control device 3 that processes a captured image output from the rigid endoscope 2B, and a display device 4 that displays an image (captured image and identification image) based on a video signal for display processed by the control device 3.

The rigid endoscope 2B corresponds to the medical observation device according to the present disclosure. As illustrated in FIG. 11, the rigid endoscope 2B includes an insertion unit 2B1 and a camera head 2B2.

The insertion unit 2B1 has an elongated shape and is entirely hard, or is partially hard and partially soft, and the insertion unit 2B1 is inserted into a living body. The insertion unit 2B1 takes in light (subject image) from the inside of the living body (subject).

The camera head 2B2 is detachably connected to a proximal end (eyepiece) of the insertion unit 2B1. The camera head 2B2 has substantially the same configuration as the microscope unit 21 described in the above-described first embodiment. Further, the camera head 2B2 captures the subject image taken in by the insertion unit 2B1 and outputs the captured image.

In the ninth embodiment, the control device 3 (control unit 33) performs determination processing different from the determination processing (Step S3) described in the first embodiment described above.

Specifically, the control unit 33 calculates a motion amount from a previous captured image to a subsequent captured image in time series by a known method (for example, a block matching method, a gradient method, or the like) based on a plurality of captured images sequentially output from the camera head 2B2. Then, in a case where the motion amount is equal to or more than a specific threshold, the control unit 33 determines that an imaging field of view of the rigid endoscope 2B has been moved. On the other hand, in a case where the motion amount is less than the specific threshold, the control unit 33 determines that the imaging field of view of the rigid endoscope 2B has not been moved.

According to the ninth embodiment described above, in addition to the same effect as that of the first embodiment described above, the following effects are obtained.

The control device 3 according to the ninth embodiment performs the above-described determination processing. Therefore, it is possible to offset an influence of camera shake due to a scopist holding the rigid endoscope 2B by hand and appropriately determine that the imaging field of view of the rigid endoscope 2B has been moved.

Tenth Embodiment

Next, a tenth embodiment will be described.

In the following description, the same components as those in the first embodiment will be designated by the same reference signs, and a detailed description thereof will be omitted or simplified.

In the first embodiment described above, the present disclosure is applied to the medical observation system 1 using a surgical microscope (medical observation device 2).

On the other hand, in the tenth embodiment, the present disclosure is applied to a medical observation system using a flexible endoscope.

Figure 12:
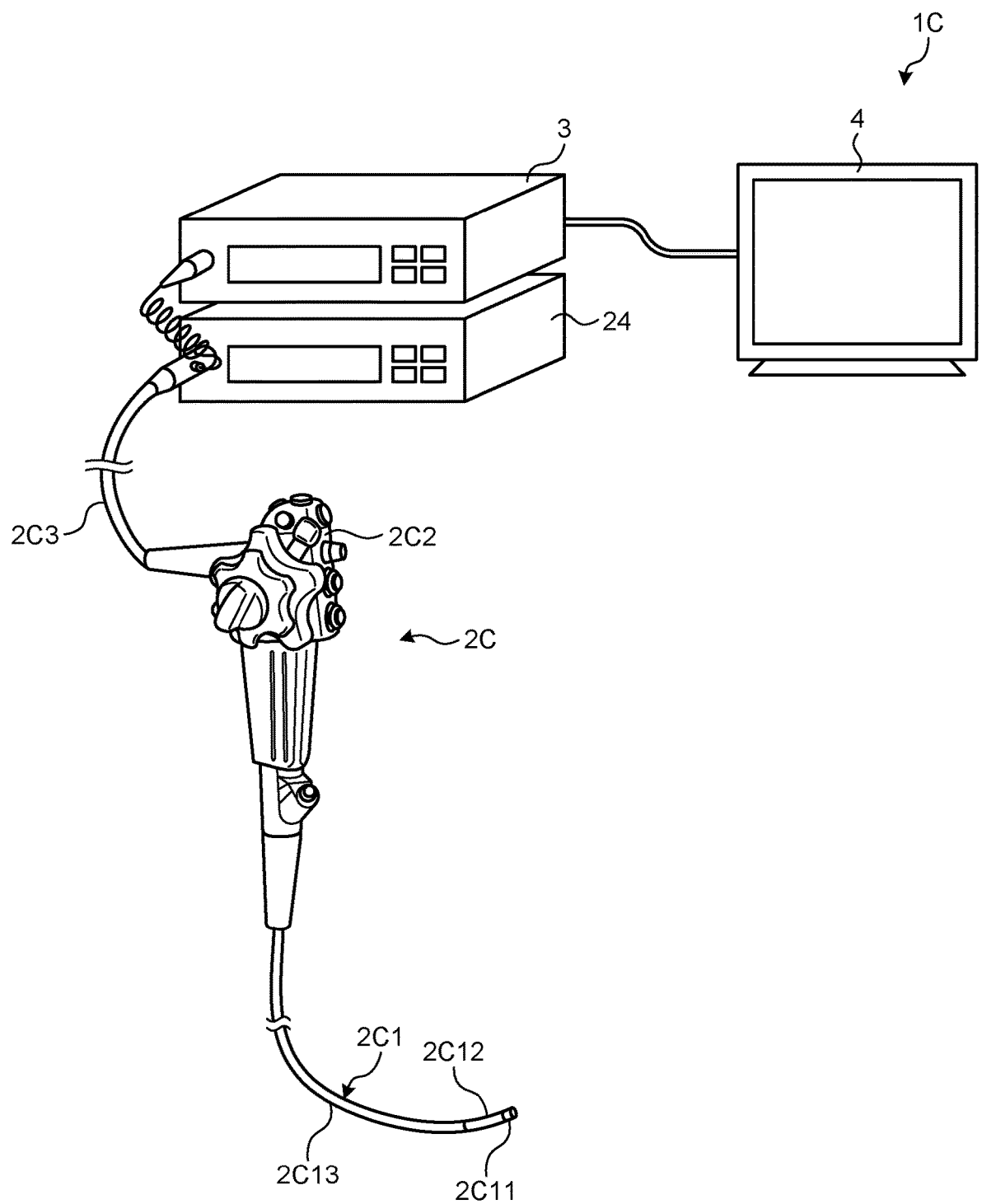
FIG. 12 is a view illustrating a medical observation system according to a tenth embodiment.

FIG. 12 is a diagram illustrating a medical observation system 1C according to the tenth embodiment.

As illustrated in FIG. 12, the medical observation system 1C according to the tenth embodiment includes a flexible endoscope 2C that captures an in-vivo image of an observed region by inserting an insertion unit 2C1 into a living body and outputs the captured image, a light source device 24 that generates illumination light emitted from a distal end of the flexible endoscope 2C, a control device 3 that processes the captured image output from the flexible endoscope 2C, and a display device 4 that displays an image (the captured image and identification image) based on a video signal for display processed by the control device 3.

The flexible endoscope 2C corresponds to the medical observation device according to the present disclosure. As illustrated in FIG. 12, the flexible endoscope 2C includes the insertion unit 2C1 that is flexible and has an elongated shape, an operating unit 2C2 that is connected to a proximal end of the insertion unit 2C1 and receives various operations, and a universal cord 2C3 that extends from the operating unit 2C2 in a direction different from a direction in which the insertion unit 2C1 extends and incorporates various cables connected to the light source device 24 and the control device 3.

As illustrated in FIG. 12, the insertion unit 2C1 includes a distal end portion 2C11, a bendable portion 2C12 that is bendable, is connected to a proximal end of the distal end portion 2C11, and includes a plurality of bending pieces, and a flexible tube portion 2C13 that is connected to a proximal end of the bendable portion 2C12, is flexible, and has an elongated shape.

Further, although not illustrated in detail, a component substantially similar to the microscope unit 21 described in the first embodiment described above is embedded in the distal end portion 2C11. Further, the captured image from the distal end portion 2C11 is output to the control device 3 via the operating unit 2C2 and the universal cord 2C3.

In the tenth embodiment, the control device 3 (control unit 33) performs the same determination processing as the determination processing (Step S3) described in the above-described the ninth embodiment.

Even in a case where the flexible endoscope 2C is used as in the tenth embodiment described above, the same effect as that of the first and ninth embodiment described above is obtained.

Other Embodiments

Although the embodiments for carrying out the present disclosure have been described so far, the present disclosure should not be limited only to the above-described first to tenth embodiments.

In the above-described the first to tenth embodiments, the specific position according to the present disclosure is the center position of the specific region, but the present disclosure is not limited thereto, and other positions may be used as long as the position is within the specific region.

In the above-described the first to tenth embodiments, the image processor 321 that performs the enlargement processing (electronic zoom) is adopted as the scaling unit according to the present disclosure, but the present disclosure is not limited thereto. The microscope units 21 and 21A may have an optical zoom function, and the control unit 33 that operates the microscope units 21 and 21A to execute the optical zoom function may serve as the scaling unit according to the present disclosure.

FIG. 13 is a diagram illustrating modifications of the first to tenth embodiments.

In the above-described the first to tenth embodiments, the index IN1 having a black cross shape is adopted as the index according to the present disclosure, but the present disclosure is not limited thereto.

For example, as in an identification image P18 illustrated in FIG. 13(*a*), an index IN2 having a hollow cross shape may be adopted.

In addition, for example, as in an identification image P19 illustrated in FIG. 13(*b*), an index IN3 having a black X shape may be adopted.

Further, for example, as in an identification image P20 illustrated in FIG. 13(*c*), an index IN4 having longer vertical and horizontal lengths than the index IN1 may be adopted.

In addition, for example, as in an identification image P21 illustrated in FIG. 13(*d*), an index IN5 having a cross shape in which four black L shapes are combined may be adopted.

Further, for example, the index is not limited to black, and an index having a cross shape of another color may be adopted. At this time, for example, as in an identification image P22 illustrated in FIG. 13(*e*), a color of an index IN6 may be an inverted color with respect to a background color.

In addition, in the above-described first to tenth embodiments, the image centers of the captured image and the identification image coincide with a screen center of the display device 4, but the present disclosure is not limited thereto, and an identification image P23 may be displayed at a position eccentric from the screen center of the display device 4 as illustrated in FIG. 13(*f*).

In the above-described first to tenth embodiments, the order of processing in the flow illustrated in FIG. 3 may be changed as long as there is no inconsistency. In addition, the technologies described in the first to tenth embodiments described above may be appropriately combined.

Note that the following configurations also fall within the technical scope of the present disclosure.

(1) A medical image processing device including: a captured image acquisition unit that acquires a captured image captured by a medical observation device; a determination unit that determines whether or not an imaging field of view in the medical observation device has been moved; and an identification image generation unit that generates, in a case where the determination unit determines that the imaging field of view has been moved, an identification image in which a specific position in a specific region displayed on a display device in an entire image region of the captured image is identifiable with respect to other positions.

(2) The medical image processing device according to (1), in which the specific position is a center position in the specific region.

(3) The medical image processing device according to (1) or (2), in which the identification image generation unit generates the identification image including a frame corresponding to a detection region for calculating an evaluation value used for controlling a focal position of an imaging unit that generates the captured image.

(4) The medical image processing device according to any one of (1) to (3), in which the identification image generation unit generates the identification image including a frame corresponding to a detection region for calculating an evaluation value used for controlling a brightness of the captured image.

(5) The medical image processing device according to any one of (1) to (4), further including a scaling unit that scales the imaging field of view or the specific region at each of a first zoom magnification and a second zoom magnification higher than the first zoom magnification, in which in a case where the scaling unit performs scaling at the first zoom magnification, the identification image generation unit generates the identification image including an observation frame indicating an observation range in a case where the scaling unit performs scaling at the second zoom magnification.

(6) The medical image processing device according to any one of (1) to (5), further including a scaling unit that scales the imaging field of view or the specific region at each of a first zoom magnification and a second zoom magnification higher than the first zoom magnification, in which in a case where the scaling unit performs scaling at the first zoom magnification, the scaling unit switches the first zoom magnification to the second zoom magnification at a timing when the determination unit determines that the imaging field of view has been moved, and switches back the second zoom magnification to the first zoom magnification at a timing when the determination unit determines that the imaging field of view has not been moved, and in a case where the determination unit determines that the imaging field of view has been moved, the identification image generation unit generates the identification image corresponding to the second zoom magnification.

(7) The medical image processing device according to any one of (1) to (5), further including a scaling unit that scales the imaging field of view or the specific region at each of a first zoom magnification and a second zoom magnification higher than the first zoom magnification, in which in a case where the scaling unit performs scaling at the second zoom magnification, the scaling unit switches the second zoom magnification to the first zoom magnification at a timing when the determination unit determines that the imaging field of view has been moved, and switches back the first zoom magnification to the second zoom magnification at a timing when the determination unit determines that the imaging field of view has not been moved, and in a case where the determination unit determines that the imaging field of view has been moved, the identification image generation unit generates the identification image corresponding to the first zoom magnification.

(8) The image processing device according to any one of (1) to (5), further including a scaling unit that scales the specific region at each of a first zoom magnification and a second zoom magnification higher than the first zoom magnification, in which the scaling unit simultaneously performs scaling at each of the first zoom magnification and the second zoom magnification at a timing when the determination unit determines that the imaging field of view has been moved, and switches back the first zoom magnification or the second zoom magnification to an original zoom magnification at a timing when the determination unit determines that the imaging field of view has not been moved, and in a case where the determination unit determines that the imaging field of view has been moved, the identification image generation unit generates a first identification image that is the identification image corresponding to the first zoom magnification and generates a second identification image that is the identification image corresponding to the second zoom magnification.

(9) The medical image processing device according to any one of (1) to (8), in which the identification image generation unit generates the identification image including an index indicating the specific position in the specific region.

(10) The medical image processing device according to (9), in which the captured image includes a left-eye captured image and a right-eye captured image having a parallax with each other, and in a case where the determination unit determines that the imaging field of view has been moved, the identification image generation unit generates a left-eye identification image that is the identification image in which the index is added in such a way as to correspond to a depth position of the specific position in the specific region in the entire image region of the left-eye captured image, and generates a right-eye identification image that is the identification image in which the index is added in such a way as to correspond to a depth position of the specific position in the specific region in the entire image region of the right-eye captured image.

(11) The medical image processing device according to (1) to (10), in which the medical observation device includes: a microscope unit that generates the captured image by imaging the subject; a support unit that rotatably supports the microscope unit around a plurality of different axes; and a posture detection unit that detects a posture of the support unit, and the determination unit determines that the imaging field of view has been moved in a case where a change amount of the posture per unit time detected by the posture detection unit is larger than 0 and equal to or less than a specific threshold.

(12) A medical image processing device including: a captured image acquisition unit that acquires a captured image captured by a medical observation device; an operating unit that receives a moving operation for an imaging field of view in the medical observation device; and an identification image generation unit that generates, in a case where the operating unit has received the moving operation, an identification image in which a specific position in a specific region displayed on a display device in an entire image region of the captured image is identifiable with respect to other positions.

(13) A medical observation system including: the medical observation device that generates the captured image by imaging a subject; the medical image processing device according to any one of (1) to (12); and a display device that displays the identification image generated by the medical image processing device.

REFERENCE SIGNS LIST 1, 1A to 1C MEDICAL OBSERVATION SYSTEM
2, 2A MEDICAL OBSERVATION DEVICE
2B RIGID ENDOSCOPE
2B1 INSERTION UNIT
2B2 CAMERA HEAD
2C FLEXIBLE ENDOSCOPE
2C1 INSERTION UNIT
2C11 DISTAL END PORTION
2C12 CURVED PORTION
2C13 FLEXIBLE TUBE PORTION
2C2 OPERATING UNIT
2C3 UNIVERSAL CODE

3 CONTROL DEVICE
4, 4A DISPLAY DEVICE
21, 21A MICROSCOPE UNIT
22 BASE UNIT
23 SUPPORT UNIT
24 LIGHT SOURCE DEVICE
25 LIGHT GUIDE
26 FOOT SWITCH
31 COMMUNICATION UNIT
32 OBSERVATION IMAGE GENERATION UNIT
33 CONTROL UNIT
34 STORAGE UNIT
211 IMAGING UNIT
211AL LEFT-EYE IMAGING UNIT
211AR RIGHT-EYE IMAGING UNIT
212 COMMUNICATION UNIT
213 DRIVING UNIT
214 DETECTION UNIT
215 BRAKE RELEASE SWITCH
221 CASTER
231a FIRST ARM
231b SECOND ARM
231c THIRD ARM
231d FOURTH ARM
231e FIFTH ARM
231f SIXTH ARM
231g SEVENTH ARM
232a FIRST JOINT
232b SECOND JOINT
232c THIRD JOINT
232d FOURTH JOINT
232e FIFTH JOINT
232f SIXTH JOINT
233 COUNTERWEIGHT
234 STATE SWITCHING UNIT
235 POSTURE DETECTION UNIT
236 ACTUATOR
261 LEVER
321 IMAGE PROCESSOR
322 DISPLAY CONTROLLER
2111 LENS UNIT
2111a FOCUS LENS
2112 DIAPHRAGM
2113 IMAGING ELEMENT
2114 SIGNAL PROCESSOR
Fr1 DETECTION FRAME
Fr2, Fr3 OBSERVATION FRAME
IN1 to IN6 INDEX
O1 FIRST AXIS
O2 SECOND AXIS
O3 THIRD AXIS
O4 FOURTH AXIS
O5 FIFTH AXIS
O6 SIXTH AXIS
P1, P3, P8, P10, P11, P13, P14, P17 CAPTURED IMAGE
P2, P4 to P7, P9, P12, P15, P16, P18 to P23 IDENTIFICATION IMAGE

The invention claimed is:

1. A medical image processing device comprising:
a captured image acquisition circuit configured to acquire a captured image captured by a medical observation device;
a determination circuit configured to determine whether or not an imaging field of view in the medical observation device has been moved; and
an identification image generation circuit configured to generate, in response to the imaging field of view having been moved, an identification image in which a specific position in a specific region displayed on a display device in an entire image region of the captured image is identifiable with respect to other positions and otherwise not generate the identification image.

2. The medical image processing device according to claim 1, wherein the specific position is a center position in the specific region.

3. The medical image processing device according to claim 1, wherein the identification image generation circuit is configured to generate the identification image including a frame corresponding to a detection region for calculating an evaluation value used for controlling a focal position of an image sensor that generates the captured image.

4. The medical image processing device according to claim 1, wherein the identification image generation circuit is configured to generate the identification image including a frame corresponding to a detection region for calculating an evaluation value used for controlling a brightness of the captured image.

5. The medical image processing device according to claim 1, further comprising a scaling circuit configured to scale the imaging field of view or the specific region at each of a first zoom magnification and a second zoom magnification higher than the first zoom magnification, wherein
in a case where the scaling circuit performs scaling at the first zoom magnification, the identification image generation circuit is configured to generate the identification image including an observation frame indicating an observation range in a case where the scaling circuit performs scaling at the second zoom magnification.

6. The medical image processing device according to claim 1, further comprising a scaling circuit configured to scale the imaging field of view or the specific region at each of a first zoom magnification and a second zoom magnification higher than the first zoom magnification, wherein
in a case where the scaling circuit performs scaling at the first zoom magnification, the scaling circuit is configured to
switch the first zoom magnification to the second zoom magnification at a timing when the determination circuit determines that the imaging field of view has been moved, and
switch back the second zoom magnification to the first zoom magnification at a timing when the determination circuit determines that the imaging field of view has not been moved, and
in a case where the determination circuit determines that the imaging field of view has been moved, the identification image generation circuit is configured to generate the identification image corresponding to the second zoom magnification.

7. The medical image processing device according to claim 1, further comprising a scaling circuit configured to scale the imaging field of view or the specific region at each of a first zoom magnification and a second zoom magnification higher than the first zoom magnification,
wherein in a case where the scaling circuit performs scaling at the second zoom magnification, the scaling circuit is configured to
switch the second zoom magnification to the first zoom magnification at a timing when the determination circuit determines that the imaging field of view has been moved, and
switch back the first zoom magnification to the second zoom magnification at a timing when the determination circuit determines that the imaging field of view has not been moved, and in a case where the determination circuit determines that the imaging field of view has been moved, the identification image generation circuit is configured to generate the identification image corresponding to the first zoom magnification.

8. The medical image processing device according to claim 1, further comprising a scaling circuit configured to scale the specific region at each of a first zoom magnification and a second zoom magnification higher than the first zoom magnification, wherein the scaling circuit is configured to simultaneously perform scaling at each of the first zoom magnification and the second zoom magnification at a timing when the determination circuit determines that the imaging field of view has been moved, and switch back the first zoom magnification or the second zoom magnification to an original zoom magnification at a timing when the determination circuit determines that the imaging field of view has not been moved, and in a case where the determination circuit determines that the imaging field of view has been moved, the identification image generation circuit is configured to generate a first identification image that is the identification image corresponding to the first zoom magnification, and generate a second identification image that is the identification image corresponding to the second zoom magnification.

9. The medical image processing device according to claim 1, wherein the identification image generation circuit is configured to generate the identification image including an index indicating the specific position in the specific region.

10. The medical image processing device according to claim 9, wherein the captured image includes: a left-eye captured image; and a right-eye captured image having a parallax with each other, and in a case where the determination circuit determines that the imaging field of view has been moved, the identification image generation circuit is configured to generate a left-eye identification image that is the identification image in which the index is added in such a way as to correspond to a depth position of the specific position in the specific region in the entire image region of the left-eye captured image, and generate a right-eye identification image that is the identification image in which the index is added in such a way as to correspond to a depth position of the specific position in the specific region in the entire image region of the right-eye captured image.

11. The medical image processing device according to claim 1, wherein the medical observation device includes:

a microscope configured to generate the captured image by imaging a subject;

a support configured to rotatably support the microscope around a plurality of different axes; and a posture detector configured to detect a posture of the support, and the determination circuit is configured to determine that the imaging field of view has been moved in a case where a change amount of the posture per unit time detected by the posture detector is larger than 0 and equal to or less than a specific threshold.

12. A medical image processing device comprising:

a captured image acquisition circuit configured to acquire a captured image captured by a medical observation device;

an operating circuit configured to receive a moving operation for an imaging field of view in the medical observation device; and an identification image generation circuit configured to generate, in response to the operating circuit receiving the moving operation, an identification image in which a specific position in a specific region displayed on a display device in an entire image region of the captured image is identifiable with respect to other positions and otherwise not generate the identification image.

13. A medical observation system comprising:

a medical observation device configured to generate a captured image by imaging a subject;

a medical image processing device according to claim 1; and a display device configured to display an identification image generated by the medical image processing device.

14. The medical observation system according to claim 13, wherein the medical observation device includes:

a microscope configured to generate the captured image by imaging a subject;

a support configured to rotatably support the microscope around a plurality of different axes; and a posture detector configured to detect a posture of the support, and the determination circuit is configured to determine that the imaging field of view has been moved in a case where a change amount of the posture per unit time detected by the posture detector is larger than 0 and equal to or less than a specific threshold.

15. The medical image processing device according to claim 12, further comprising a scaling circuit configured to scale the imaging field of view or the specific region at each of a first zoom magnification and a second zoom magnification higher than the first zoom magnification, wherein in a case where the scaling circuit performs scaling at the first zoom magnification, the scaling circuit is configured to switch the first zoom magnification to the second zoom magnification at a timing when the operating circuit has received the moving operation, and switch back the second zoom magnification to the first zoom magnification at a timing when the operating circuit has not been received the moving operation, and in response to the operating circuit receiving the moving operation, the identification image generation circuit is configured to generate the identification image corresponding to the second zoom magnification.

16. The medical image processing device according to claim 12, further comprising a scaling circuit configured to scale the imaging field of view or the specific region at each of a first zoom magnification and a second zoom magnification higher than the first zoom magnification, wherein in a case where the scaling circuit performs scaling at the second zoom magnification, the scaling circuit is configured to switch the second zoom magnification to the first zoom magnification at a timing when the operating circuit has received the moving operation, and switch back the first zoom magnification to the second zoom magnification at a timing when the operating circuit has not received the moving operation, and in response to the operating circuit receiving the moving operation, the identification image generation circuit is configured to generate the identification image corresponding to the first zoom magnification.

17. The medical image processing device according to claim 12, further comprising a scaling circuit configured to scale the specific region at each of a first zoom magnification and a second zoom magnification higher than the first zoom magnification, wherein the scaling circuit is configured to simultaneously perform scaling at each of the first zoom magnification and the second zoom magnification at a timing when the operating circuit has received the moving operation, and switch back the first zoom magnification or the second zoom magnification to an original zoom magnification at a timing when the operating circuit has not received the moving operation, and in response to the operating circuit receiving the moving operation, the identification image generation circuit is configured to generate a first identification image that is the identification image corresponding to the first zoom magnification, and generate a second identification image that is the identification image corresponding to the second zoom magnification.

18. A non-transitory computer readable storage device having computer readable instructions that when executed by circuitry cause the circuitry to:

acquire a captured image captured by a medical observation device;

determine whether or not an imaging field of view in the medical observation device has been moved; and generate, in response to the imaging field of view having been moved, an identification image in which a specific position in a specific region displayed on a display device in an entire image region of the captured image is identifiable with respect to other positions and otherwise not generate the identification image.

19. The transitory computer readable storage device according to claim 18, wherein the circuitry is further caused to:

scale the imaging field of view or the specific region at each of a first zoom magnification and a second zoom magnification higher than the first zoom magnification, wherein for the first zoom magnification, switch the first zoom magnification to the second zoom magnification at a timing when the imaging field of view has been moved, and switch back the second zoom magnification to the first zoom magnification at a timing when the imaging field of view has not been moved, and in response to the imaging field of view having been moved, generate the identification image corresponding to the second zoom magnification.

20. The transitory computer readable storage device according to claim 18, wherein the captured image includes a left-eye captured image; and a right-eye captured image having a parallax with each other and the imaging field of view has been moved, the circuitry is further caused to:

generate a left-eye identification image that is the identification image in which an index indicating the specific position in the specific region is added in such a way as to correspond to a depth position of the specific position in the specific region in the entire image region of the left-eye captured image, and generate a right-eye identification image that is the identification image in which an index indicating the specific position in the specific region is added in such a way as to correspond to a depth position of the specific position in the specific region in the entire image region of the right-eye captured image.

* * * * *